(12) United States Patent
Takemoto

(10) Patent No.: US 11,497,853 B2
(45) Date of Patent: Nov. 15, 2022

(54) LIQUID MEDICINE ADMINISTRATION DEVICE AND GASKET BIASING MEMBER ASSEMBLY

(71) Applicant: TERUMO KABUSHIKI KAISHA, Tokyo (JP)

(72) Inventor: Masafumi Takemoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 493 days.

(21) Appl. No.: 16/586,810

(22) Filed: Sep. 27, 2019

(65) Prior Publication Data

US 2020/0023131 A1  Jan. 23, 2020

Related U.S. Application Data

(63) Continuation of application No. PCT/JP2018/010346, filed on Mar. 15, 2018.

(30) Foreign Application Priority Data

Mar. 31, 2017  (JP) .............................. JP2017-073255

(51) Int. Cl.
*A61M 5/20* (2006.01)
*A61M 5/31* (2006.01)
*A61M 5/32* (2006.01)

(52) U.S. Cl.
CPC ........ *A61M 5/2033* (2013.01); *A61M 5/3135* (2013.01); *A61M 5/3202* (2013.01); *A61M 2005/3131* (2013.01)

(58) Field of Classification Search
CPC .............. A61M 5/2033; A61M 5/3135; A61M 5/3202; A61M 5/20; A61M 5/28; A61M 5/281; A61M 2005/3131
See application file for complete search history.

(56) References Cited

U.S. PATENT DOCUMENTS 5,658,259 A  8/1997  Pearson et al.
6,203,530 B1  3/2001  Stewart, Sr.
(Continued)

FOREIGN PATENT DOCUMENTS

CN  102614564 A  8/2012
CN  103596612 A  2/2014
(Continued)

OTHER PUBLICATIONS

International Searching Authority, "International Search Report," issued in connection with International Patent Application No. PCT/JP2018/010346, dated May 1, 2018.
(Continued)

*Primary Examiner* — James D Ponton
*Assistant Examiner* — Neeraja Gollamudi
(74) *Attorney, Agent, or Firm* — Foley & Lardner LLP

(57) ABSTRACT

A liquid medicine administration device includes a prefilled syringe and a gasket biasing member assembly. The biasing member assembly includes: a gasket pressing member configured to press a gasket; a flange attachment member attached to the prefilled syringe; a biasing member housed between the pressing member and the flange attachment member; and an operating member including an engagement holding portion. The pressing member includes an engagement portion to be engaged with the flange attachment member. When the engagement holding portion is located at an abutment position, deformation of a deformable portion is inhibited by abutment between the engagement holding portion and an abutment portion of a deformable portion, and engagement between the engagement portion and the attachment member body portion is held.

17 Claims, 25 Drawing Sheets

(56) References Cited

U.S. PATENT DOCUMENTS

| | | | |
|---|---|---|---|
| 9,125,996 B2 | 9/2015 | Takemoto | |
| 2005/0222539 A1* | 10/2005 | Gonzales | A61M 5/2033 604/207 |
| 2007/0027430 A1 | 2/2007 | Hommann | |
| 2012/0016296 A1* | 1/2012 | Charles | A61M 5/2066 604/87 |
| 2017/0080159 A1 | 3/2017 | Wei | |

FOREIGN PATENT DOCUMENTS

| | | |
|---|---|---|
| JP | 2007-514487 A | 6/2007 |
| WO | WO-2005/097238 A2 | 10/2005 |
| WO | WO-2015/160600 A1 | 10/2015 |
| WO | WO-2016/180967 A | 11/2016 |
| WO | WO-2017/017360 A1 | 2/2017 |

OTHER PUBLICATIONS

International Searching Authority, "Written Opinion," issued in connection with International Patent Application No. PCT/JP2018/010346, dated May 1, 2018.
Chinese Office Action dated Apr. 8, 2021 in China Application No. 201880022577.
International Searching Authority, "International Search Report" and "Written Opinion" issued in connection with International Patent Application No. PCT/JP2018/010346, dated May 1, 2018.
Extended European Search Report dated Mar. 17, 2021 in corresponding European Patent Application No. 18777947.5.

* cited by examiner

LIQUID MEDICINE ADMINISTRATION DEVICE AND GASKET BIASING MEMBER ASSEMBLY

CROSS-REFERENCE TO RELATED APPLICATIONS

This is a bypass continuation of PCT Application No. PCT/JP2018/010346, filed on Mar. 15, 2018, which claims priority to Japanese Application No. 2017-073255, filed on Mar. 31, 2017. The contents of these applications are hereby incorporated by reference in their entireties.

BACKGROUND

The present disclosure relates to liquid medicine administration device to administer liquid medicine into a living body and a gasket biasing member assembly that biases a gasket of a syringe in a distal end direction to move the gasket in the distal end direction.

There is a conventionally-known prefilled syringe that is prefilled with liquid such as liquid medicine. The prefilled syringe includes an outer cylinder containing the liquid medicine, an injection needle provided at a discharge port of the outer cylinder, a gasket slidable inside the outer cylinder, and a plunger to press the gasket in a distal end direction.

The prefilled syringe may be used for self-administration, and the self-administration itself is not easy. Also, the prefilled syringe may contain viscous liquid medicine, and there may be a case where injection resistance is high, and not only the self-administration but also administration by a medical worker is not easy.

For example, WO 2015/160600 A1 (US 2017-080159 A1) discloses an injector that assists administration by utilizing force of a spring. This injector includes a connector having a distal end and a proximal end; a piston rod locked inside the connector before medication injection; a spring adapted to bias the piston rod toward the distal end; a releasable restraining means that moves the piston rod toward the distal end by force of the spring at the time of releasing the releasable restraining means; an activation means adapted to release the releasable restraining means at the time of releasing the releasable restraining means; and an attachment means to attach a syringe to the distal end of the connector.

SUMMARY

Additionally, according to a technology disclosed in WO 2015/160600 A1, a piston rod 104 is locked as illustrated in FIG. 4 of WO 2015/160600 A1. The piston rod 104 holds the locked state against biasing force of a spring 103 by a deflectable latch formed between a claw portion 104a of the piston rod 104 and a claw portion 102d of a connector 102.

However, in engagement between the claw portion 104a of the piston rod 104 and the claw portion 102d of the connector 102, opposing force against the spring is low, and there is a high possibility that the engagement is released before use. Additionally, in a case of having an engagement state having the sufficient opposing force against the spring, it becomes difficult to release the engagement.

Embodiments of the present invention include: a liquid medicine administration device that includes a compressed biasing member to discharge liquid medicine by utilizing biasing force, is further capable of surely holding the biasing force until use, allows for easy release of the held biasing force during the use, and capable of easily performing the discharge operation of the liquid medicine or assisting the same; and a gasket biasing member assembly that biases a gasket of a syringe in a distal end direction to move the gasket in the distal end direction.

According to one embodiment, a liquid medicine administration device includes: a prefilled syringe that includes an outer cylinder, liquid medicine filled inside the outer cylinder, and a gasket slidably housed inside the outer cylinder; and a biasing member assembly that biases the gasket in a distal end direction in order to discharge the liquid medicine, in which the outer cylinder includes: a liquid medicine discharge portion provided at a distal end portion of the outer cylinder; and a flange provided at a proximal end portion of the outer cylinder. The biasing member assembly includes: a gasket pressing member capable of pressing the gasket in the distal end direction; a flange attachment member attached to the flange of the outer cylinder; a biasing member to bias the gasket pressing member in the distal end direction with respect to the flange attachment member; and an operating member arranged in a manner displaceable with respect to the gasket pressing member. The gasket pressing member includes: a gasket pressing portion having, in a distal end portion, a pressing body portion capable of pressing the gasket in the distal end direction; and a deformable portion extending from the gasket pressing portion in a proximal end direction. The flange attachment member includes an attachment member body portion having a through hole into which the deformable portion is inserted. The deformable portion includes: an engagement portion arranged at a proximal end portion of the deformable portion and engaged with the attachment member body portion; and an abutment portion arranged at a position different from the engagement portion and capable of abutting on the operating member, and the biasing member is arranged in a compressed state between the gasket pressing member and the flange attachment member by engagement between the engagement portion of the deformable portion and the attachment member body portion of the flange attachment member. The engagement between the engagement portion of the deformable portion and the attachment member body portion can be released by deformation of the deformable portion. The operating member includes: an engagement holding portion that is displaceable from an abutment position to abut on the abutment portion of the deformable portion to a separation position to be separated from the abutment portion; and an operating portion to displace the operating member with respect to the gasket pressing member such that the engagement holding portion is displaced from the abutment position to the separation position, the deformation of the deformable portion is inhibited by abutment between the engagement holding portion located at the abutment position and the abutment portion of the deformable portion, and the engagement between the engagement portion of the deformable portion and the attachment member body portion is held. The deformation of the deformable portion is allowed by displacing the engagement holding portion from the abutment position to the separation position by operating the operating portion, and the deformable portion is deformed and the engagement between the engagement portion of the deformable portion and the attachment member body portion is released by biasing force of the biasing member received by the gasket pressing member.

According to another embodiment, a gasket biasing member assembly is provided. The gasket biasing member assembly is configured to bias a gasket of a syringe in a distal end direction in order to move the gasket in the distal end direction, the syringe including: an outer cylinder having a flange at a proximal end portion, and the gasket slidably housed inside the outer cylinder. The biasing member assembly includes: a gasket pressing member capable of pressing the gasket in the distal end direction; a flange attachment member attached to the flange of the outer cylinder; a biasing member to bias the gasket pressing member in the distal end direction with respect to the flange attachment member; and an operating member arranged in a manner displaceable with respect to the gasket pressing member. The gasket pressing member includes: a gasket pressing portion having, in a distal end portion, a pressing body portion capable of pressing the gasket in the distal end direction; and a deformable portion extending from the gasket pressing portion in a proximal end direction. The flange attachment member includes an attachment member body portion having a through hole into which the deformable portion is inserted. The deformable portion includes: an engagement portion arranged at a proximal end portion of the deformable portion and engaged with the attachment member body portion; and an abutment portion arranged at a position different from the engagement portion, and the biasing member is arranged in a compressed state between the gasket pressing member and the flange attachment member by engagement between the engagement portion of the deformable portion and the attachment member body portion of the flange attachment member. The engagement between the engagement portion of the deformable portion and the attachment member body portion can be released by deformation of the deformable portion. The operating member includes: an engagement holding portion that is displaceable from an abutment position to abut on the abutment portion of the deformable portion to a separation position to be separated from the abutment portion; and an operating portion to displace the operating member with respect to the gasket pressing member such that the engagement holding portion is displaced from the abutment position to the separation position, the deformation of the deformable portion is inhibited by abutment between the engagement holding portion located at the abutment position and the abutment portion of the deformable portion, and the engagement between the engagement portion of the deformable portion and the attachment member body portion is held. The deformation of the deformable portion is allowed by displacing the engagement holding portion from the abutment position to the separation position by operating the operating portion, and the deformable portion is deformed and the engagement between the engagement portion of the deformable portion and the attachment member body portion is released by biasing force of the biasing member received by the gasket pressing member.

DETAILED DESCRIPTION

Figure 1:
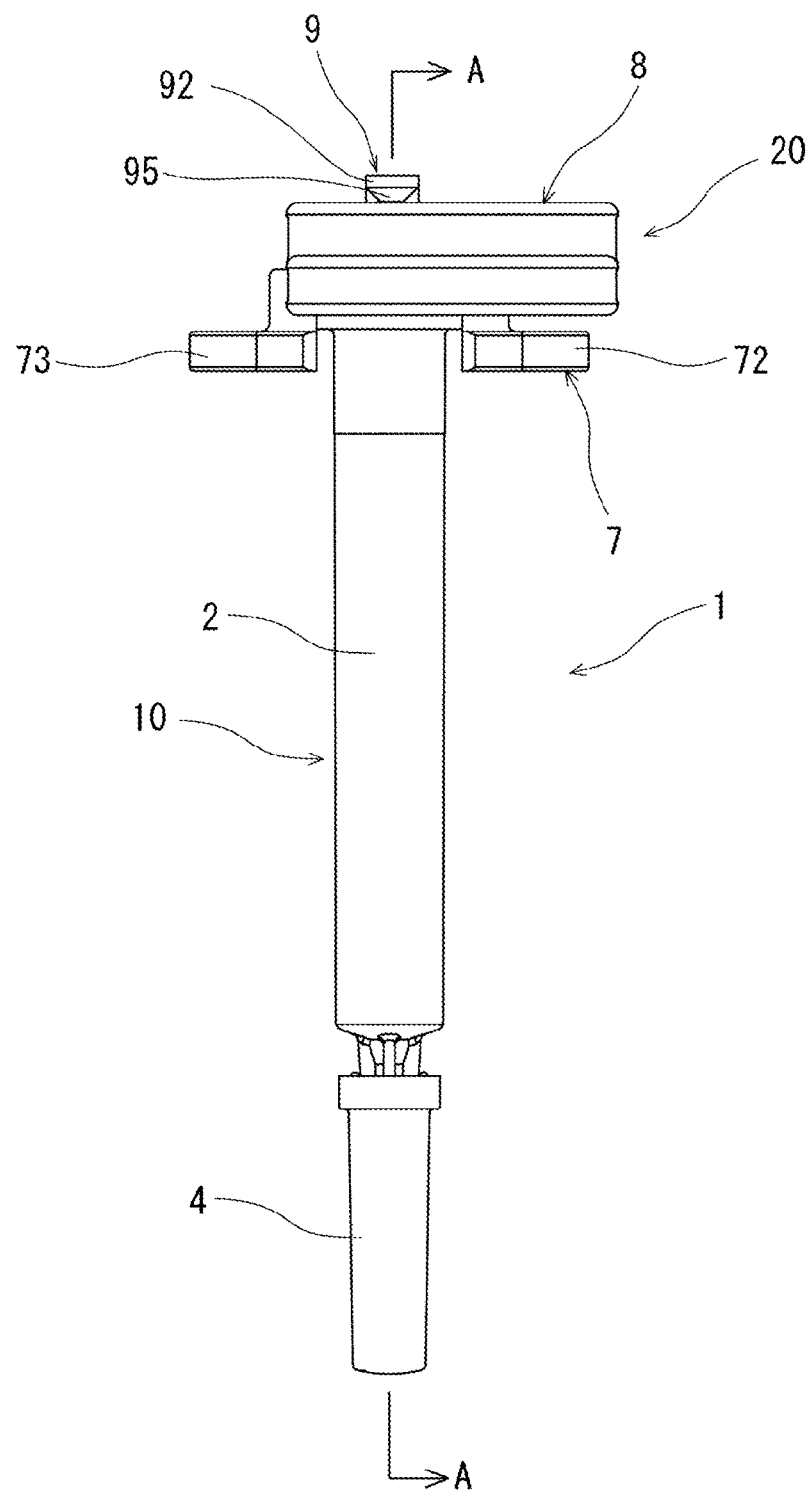
FIG. 1 is a front view of a liquid medicine administration device according to an embodiment of the present invention.
Figure 2:
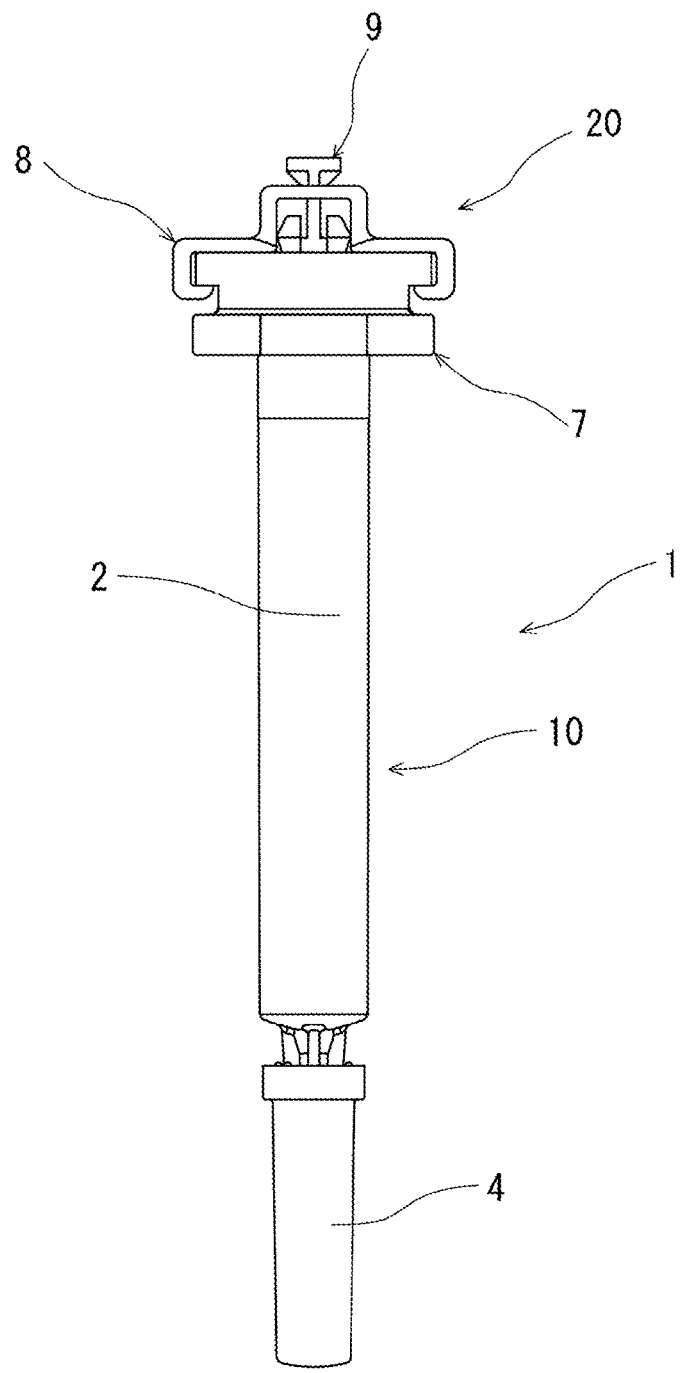
FIG. 2 is a left side view of the liquid medicine administration device illustrated in FIG. 1.
Figure 3:
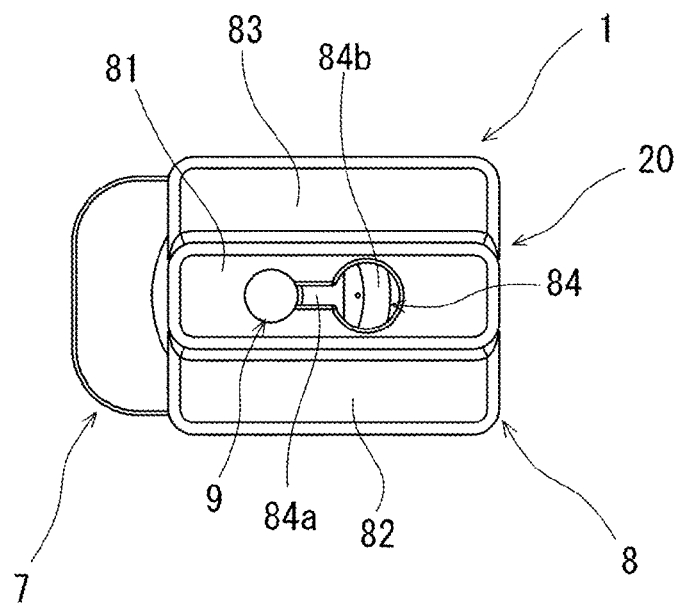
FIG. 3 is a plan view of the liquid medicine administration device illustrated in FIG. 1.
Figure 4:
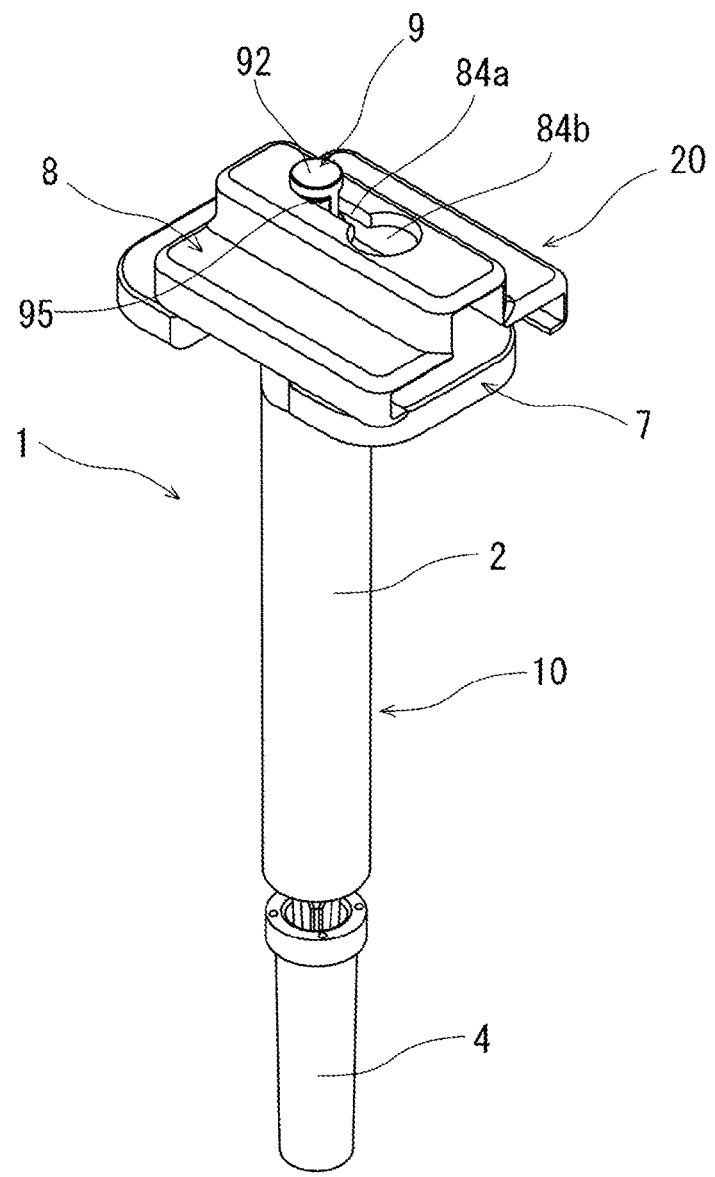
FIG. 4 is a perspective view of the liquid medicine administration device illustrated in FIG. 1 in a view from above.

Embodiments of a liquid medicine administration device and a gasket biasing member assembly of the present invention will be described with reference to the drawings.

A liquid medicine administration device 1 according to an embodiment of the present invention includes: a prefilled syringe 10 including an outer cylinder 2, liquid medicine 12 filled inside the outer cylinder 2, and a gasket 3 slidably housed inside the outer cylinder 2; and a gasket biasing member assembly 20 that biases the gasket 3 in a distal end direction in order to discharge the liquid medicine 12.

The outer cylinder 2 includes: a liquid medicine discharge portion provided at a distal end portion of the outer cylinder 2; and a flange 23 provided at a proximal end portion of the outer cylinder 2.

The gasket biasing member assembly 20 according to an embodiment of the present invention includes: a gasket pressing member 5 capable of pressing the gasket 3 in the distal end direction; a biasing member 6 to bias a flange attachment member 7 attached to the flange 23 of the outer cylinder 2 and the gasket pressing member 5 in a distal end direction with respect to the flange attachment member 7; and an operating member 9 arranged in a manner displaceable with respect to the gasket pressing member 5.

The gasket pressing member 5 includes: a gasket pressing portion 51 having a distal end portion provided with a pressing body portion 52 capable of pressing the gasket 3 in the distal end direction; and a deformable portion 53 extending from the gasket pressing portion 51 in a proximal end direction. The flange attachment member 7 includes an attachment member body portion 71 having a through hole 77 into which the deformable portion 53 is inserted. The deformable portion 53 includes: an engagement portion 541 arranged at a proximal end portion of the deformable portion 53 and engaged with the attachment member body portion 71; and an abutment portion 542 arranged at a position different from the engagement portion 541 and capable of abutting on the operating member 9. The biasing member 6 is arranged in a compressed state between the gasket pressing member 5 and the flange attachment member 7 by engagement between the engagement portion 541 of the deformable portion 53 and the attachment member body portion 71 of the flange attachment member 7. The engagement between the engagement portion 541 of the deformable portion 53 and the attachment member body portion 71 can be released by deformation of the deformable portion 53.

The operating member 9 includes: an engagement holding portion 93 that can be displaced from an abutment position to abut on the abutment portion 542 of the deformable portion 53 to a separation position to be separated from the abutment portion 542; and an operating portion 92 to displace the operating member 9 with respect to the gasket pressing member 5 such that the engagement holding portion 93 is displaced from the abutment position to the separation position. Deformation of the deformable portion 53 is inhibited by the abutment between the engagement holding portion 93 at the abutment position and the abutment portion 542 of the deformable portion 53, and the engagement between the engagement portion 541 of the deformable portion 53 and the attachment member body portion 71 is held.

Furthermore, deformation of the deformable portion 53 is allowed (is made possible) by displacing the engagement holding portion 93 from the abutment position to the separation position by operating the operating portion 92, the deformable portion 53 is deformed by biasing force of the biasing member 6 received by the gasket pressing member 5, and the engagement between the engagement portion 541 of the deformable portion 53 and the attachment member body portion 71 is released.

The liquid medicine administration device 1 of an embodiment illustrated in FIGS. 1 to 24 will be described.

The liquid medicine administration device 1 of the present embodiment includes the prefilled syringe 10 and the gasket biasing member assembly 20 attached to the prefilled syringe 10. In the liquid medicine administration device 1 and the biasing member assembly 20 of the present embodiment, movement of the gasket pressing member 5 by the biasing member 6 is inhibited by the operating member 9 including the engagement holding portion 93 that engages the engagement portion 541 of the gasket pressing member 5 with the flange attachment member 7 and abuts on the abutment portion 542 of the deformable portion 53.

Figure 5:
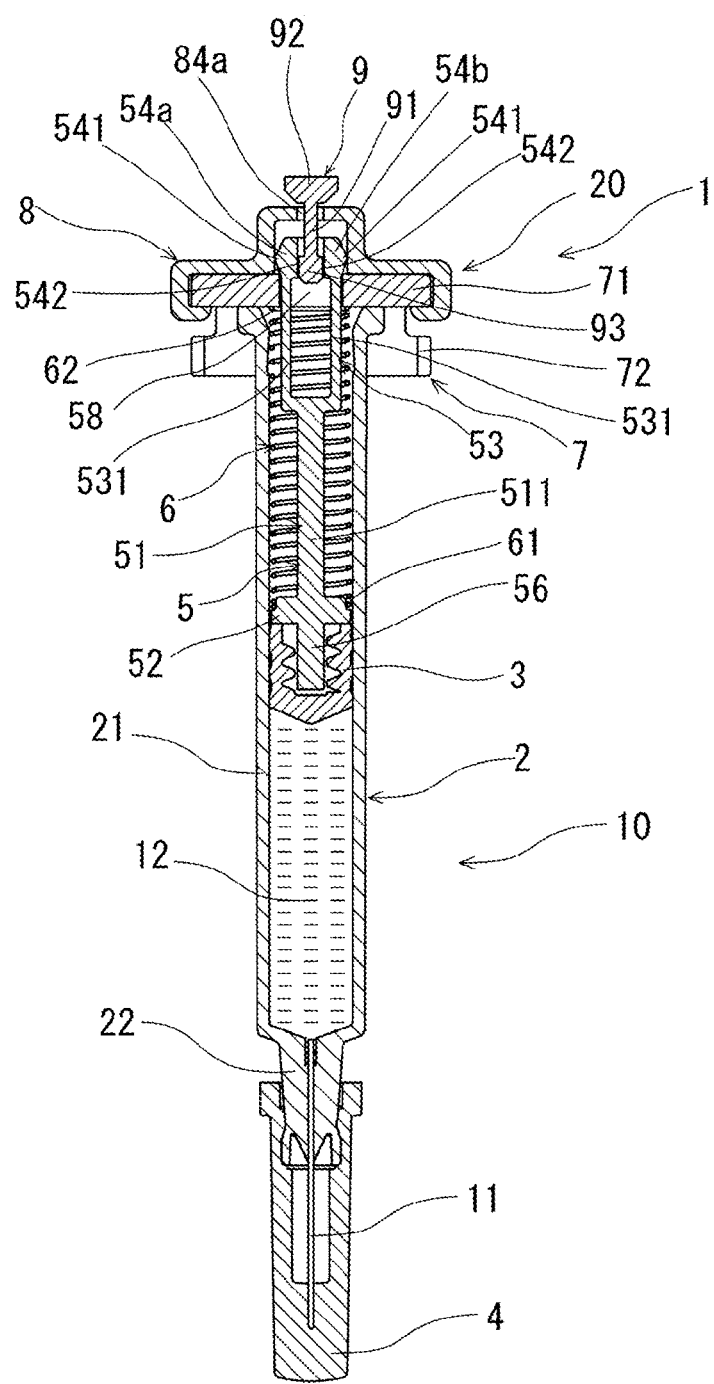
FIG. 5 is a cross-sectional view taken along a line A-A of FIG. 1.
Figure 9:
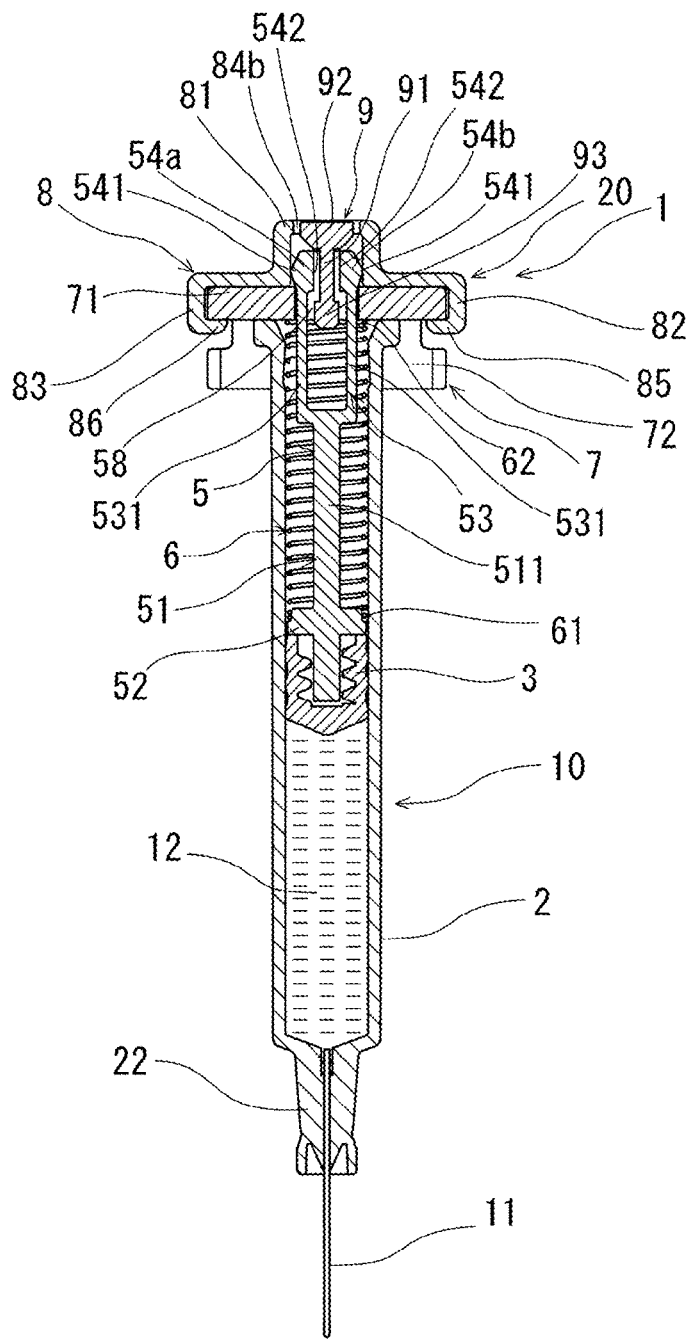
FIG. 9 is an explanatory view to describe the operation of the liquid medicine administration device illustrated in FIG. 1.
Figure 10:
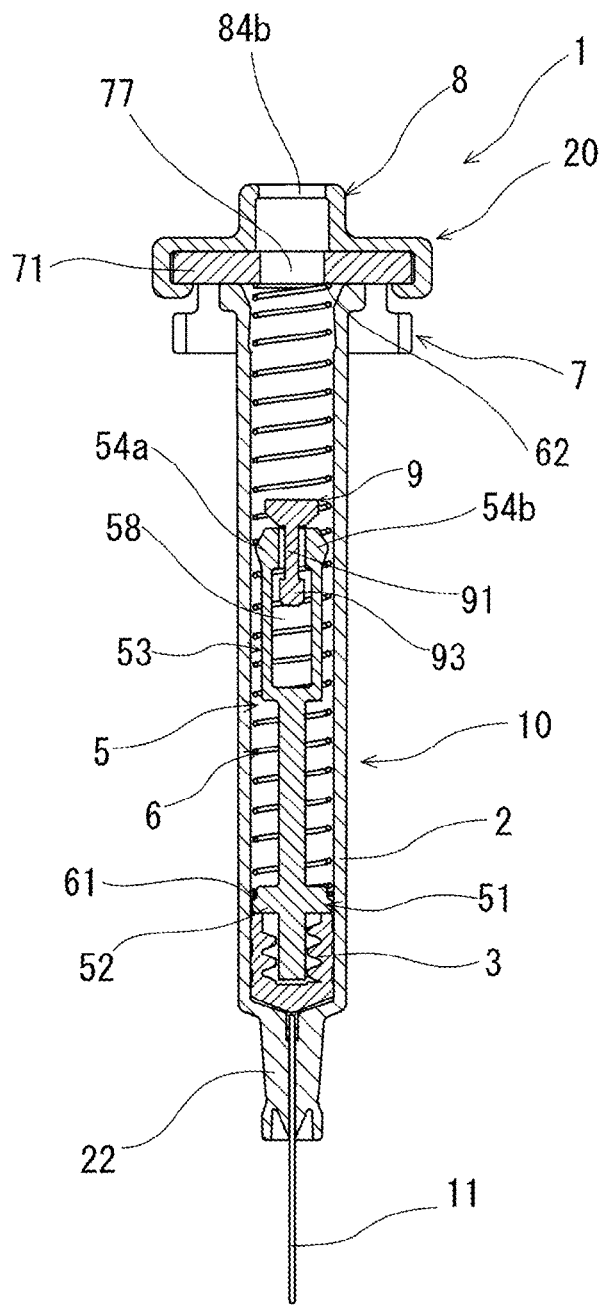
FIG. 10 is an explanatory view to describe the operation of the liquid medicine administration device illustrated in FIG. 1.

Additionally, in the liquid medicine administration device 1 of the present embodiment, deformation of the deformable portion 53 of the gasket pressing member 5 is inhibited by arranging the engagement holding portion 93 of the operating member 9 at the abutment position to abut on the abutment portion 542 of the deformable portion 53 (engagement portion 541) of the gasket pressing member 5 as illustrated in FIG. 5. Since the deformation of the deformable portion 53 is inhibited, the engagement between the engagement portion 541 of the gasket pressing member 5 and the attachment member body portion 71 of the flange attachment member 7 is held. Furthermore, as illustrated in FIG. 9, when the operating member 9 is operated to displace the engagement holding portion 93 from the abutment position to the separation position and releases the abutment between the engagement holding portion 93 and the abutment portion 542 of the deformable portion 53, the deformable portion 53 becomes deformable, the deformable portion 53 is deformed by the biasing force of the biasing member 6, and the engagement between the engagement portion 541 of the gasket pressing member 5 and the attachment member body portion 71 of the flange attachment member 7 is automatically released. Then, the gasket pressing member 5 presses and moves the gasket in a discharge direction of the liquid medicine 12 by the biasing force of the biasing member 6. Additionally, in the liquid medicine administration device 1 of the present embodiment, as illustrated in FIG. 10, the operating member 9 is moved together with the gasket pressing member 5 when the gasket pressing member 5 is moved in the distal end direction with respect to the flange attachment member 7 by the biasing force of the biasing member 6.

As the prefilled syringe 10, a known one can be used. The prefilled syringe 10 used in the present embodiment includes; the outer cylinder 2 having a needle; a sealing member (sealing cap) 4 that seals a distal end portion of an injection needle 11 of the outer cylinder having the needle; the liquid medicine 12 filled inside the outer cylinder 2 having the needle; and the gasket 3 slidable inside the outer cylinder. Therefore, in the liquid medicine administration device of the present embodiment, the injection needle 11 fixed to the distal end portion of the outer cylinder 2 of the prefilled syringe 10 constitutes the liquid medicine discharge portion, and the prefilled syringe is sealed by the sealing member (sealing cap) 4 that seals the distal end portion of the injection needle 11.

Figure 31:
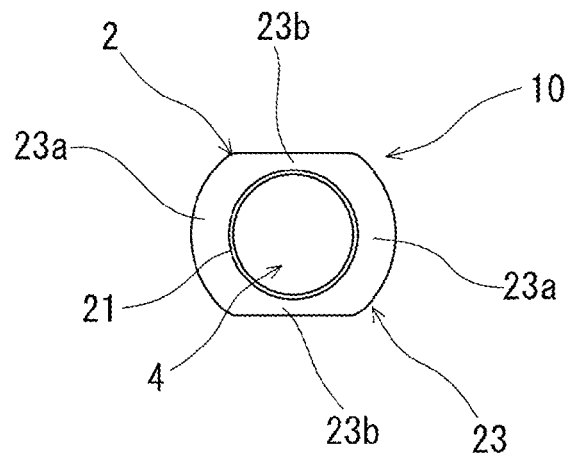
FIG. 31 is an enlarged bottom view of a prefilled syringe used in the liquid medicine administration device illustrated in FIG. 1.

Furthermore, as illustrated in FIGS. 9 to 11, and FIG. 31, the outer cylinder 2 having the needle includes: an outer cylinder body portion 21 having a substantially cylindrical shape; a needle fixing portion 22 provided at a distal end portion of the outer cylinder body portion 21; and an annular flange 23 provided at a proximal end portion of the outer cylinder body portion 21. The annular flange 23 protrudes outward from a side surface of the outer cylinder body portion 21. Additionally, as illustrated in FIG. 31, the flange 23 includes: two long extending portions 23a facing each other; and two short extending portions 23b facing each other. In the present embodiment, an outer edge of each long extending portion 23a is arcuate, and an outer edge of each short extending portion 23b is linear.

The injection needle 11 has a puncture needle tip at a distal end thereof, and a proximal end portion thereof is inserted into and fixed to the needle fixing portion 22 of the outer cylinder 2. The outer cylinder 2 includes: the injection needle 11; and the gasket 3 that is housed inside the outer cylinder 2 and slidable inside the outer cylinder 2 in a liquid-tight state. The gasket 3 is formed of an elastic body and liquid-tightly slidable inside the outer cylinder body portion 21.

As a forming material of the outer cylinder 2, glass or plastic can be used, but using the plastic is preferable, and examples of the plastic can include various kinds of resins such as polypropylene, polyethylene, polystyrene, polyamide, polycarbonate, polyvinyl chloride, poly-(4-methylpentene-1), an acrylic resin, an acrylonitrile-butadiene-styrene copolymer, polyester like polyethylene terephthalate, cyclic olefin polymer, and a cyclic olefin copolymer. Among these, the resins such as the polypropylene, the cyclic olefin polymer, and the cyclic olefin copolymer are preferable because these resins are easily molded, have excellent transparency, has no influence on the liquid medicine, and are heat resistant.

A material constituting the gasket is preferably an elastic material. The elastic material is not particularly limited, but examples thereof can include various kinds of rubber materials (particularly, those vulcanized) such as natural rubber, isoprene rubber, butyl rubber, chloroprene rubber, nitrile-butadiene rubber, styrene-butadiene rubber, and silicone rubber, a styrenic elastomer, a hydrogenated styrenic elastomer, and mixtures obtained by mixing, with these styrenic elastomers, polyolefins such as polyethylene, polypropylene, polybutene, an α-olefin copolymer, liquid paraffin, oil such as process oil, or powder inorganic substances such as talc, cast, and mica. Furthermore, it is possible to use, as the constituent material, a polyvinyl chloride elastomer, an olefin elastomer, a polyester elastomer, a polyamide elastomer, a polyurethane elastomer, or a mixture thereof.

As illustrated in FIG. 5, the sealing cap 4 includes: a closed distal end portion; an open proximal end portion; a hollow portion including a housing portion for the needle fixing portion located more on a distal end side than the open proximal end portion and housing the needle fixing portion 22 and an injection needle housing portion continuous to a tip of the housing portion for the needle fixing portion; and a needle insertable portion where the puncture needle tip of the injection needle 11 housed in an injection needle housing portion can be inserted; and a protrusion formed on an inner surface of the housing portion for the needle fixing portion. When the sealing cap 4 is attached to the needle fixing portion 22 of the outer cylinder 2, the puncture needle tip is inserted into the needle insertable portion of the sealing cap to provide sealing. Furthermore, the protrusion is engaged with an annular recess of the needle fixing portion 22 of the outer cylinder 2, and an inner surface of the housing portion for the needle fixing portion and an outer surface of the needle fixing portion are brought into a close contact state.

As a material forming the sealing cap 4, at least the needle insertable portion needs to be formed of an elastic material into which the injection needle can be inserted. Examples of the elastic material into which the injection needle can be inserted include preferably rubber such as butyl rubber, isoprene rubber, latex rubber, and silicone rubber, synthetic resin elastomers (e.g., elastomers such as styrenic elastomers like an SBS elastomer and an SEBS elastomer, olefinic elastomers like an ethylene-α-olefin copolymer elastomer, and the like.

Figure 11:
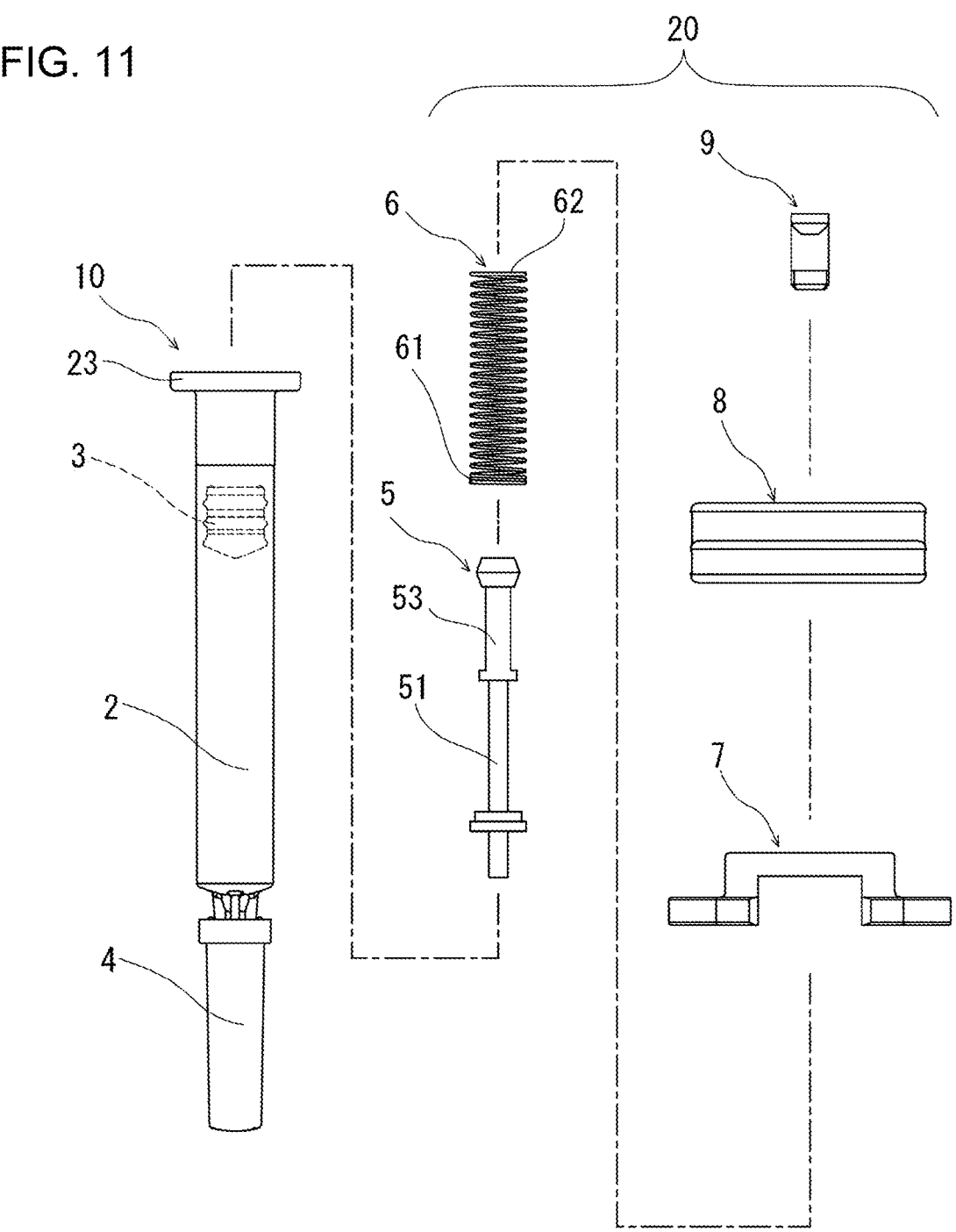
FIG. 11 is an exploded view of the liquid medicine administration device illustrated in FIG. 1.
Figure 33:
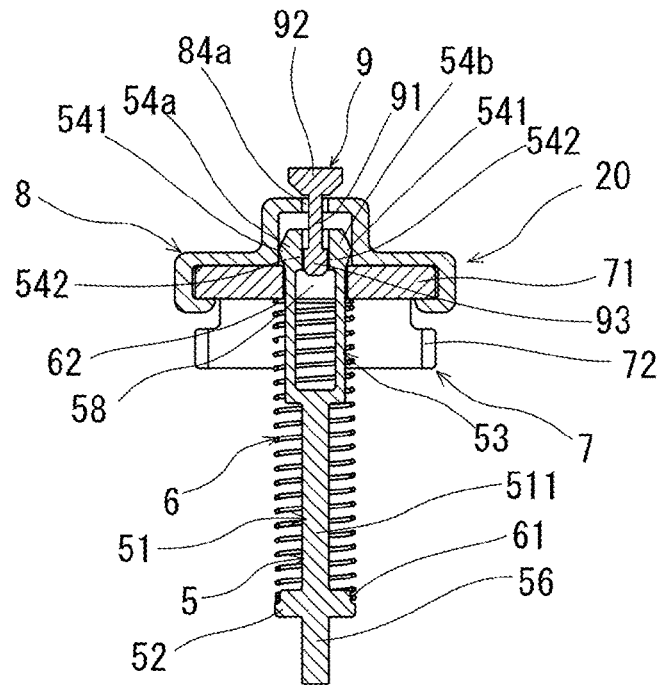
FIG. 33 is a longitudinal sectional view of the gasket biasing member assembly illustrated in FIG. 32.

In the liquid medicine administration device 1 of the present embodiment, the gasket biasing member assembly 20 attached to the prefilled syringe 10 includes, as illustrated in FIGS. 11 and 33: the gasket pressing member 5; the flange attachment member 7; the biasing member 6 arranged in the compressed state between the gasket pressing member 5 and the flange attachment member 7; the operating member 9 including the engagement holding portion 93; and an operation inhibiting member 8 that inhibits operation of the operating member 9.

Additionally, in the liquid medicine administration device 1 of the present embodiment, as illustrated in FIG. 9, the engagement holding portion 93 of the operating member 9 is displaced from the abutment position to the separation position by pushing the operating member 9 in the distal end direction with respect to the gasket pressing member 5, thereby releasing the abutment between the engagement holding portion 93 of the operating member 9 and the abutment portion 542 of the gasket pressing member 5. Specifically, in the liquid medicine administration device 1 of the present embodiment, the engagement holding portion 93 passes between two of the abutment portions 542 of the gasket pressing member 5, and is separated from the abutment portions 542 by pushing in the operating member 9. Furthermore, in the liquid medicine administration device 1 of the present embodiment, the engagement holding portion 93 is separated from the abutment portions 542 of the gasket pressing member 5 and the abutment between the engagement holding portion 93 and the abutment portions 542 can be released also by pulling out the operating member 9.

As illustrated in FIGS. 1 to 10, the flange attachment member 7 is attached to the flange 23 of the outer cylinder 2. As illustrated in FIG. 8 and FIGS. 15 to 18, the flange attachment member 7 includes the attachment member body portion 71 having the through hole 77. The through hole 77 is provided at a center of the attachment member body portion 71. The proximal end portion of the deformable portion 53 can be inserted into the through hole 77. Additionally, the through hole 77 allows the deformed deformable portion 53 and the operating member 9 to pass through the through hole. Furthermore, the through hole 77 does not allow passage of the deformable portion 53 in which deformation is inhibited by the abutment between the engagement holding portion 93 of the operating member 9 and the abutment portion 542 of the gasket pressing member 5. Moreover, the flange attachment member 7 includes two flange gripping portions 72 and 73 provided at ends of both side portions of the attachment member body portion 71, and an outer cylinder inserting portion 74 into which the proximal end portion of the outer cylinder 2 is inserted is formed between the two flange gripping portions 72 and 73.

Figure 8:
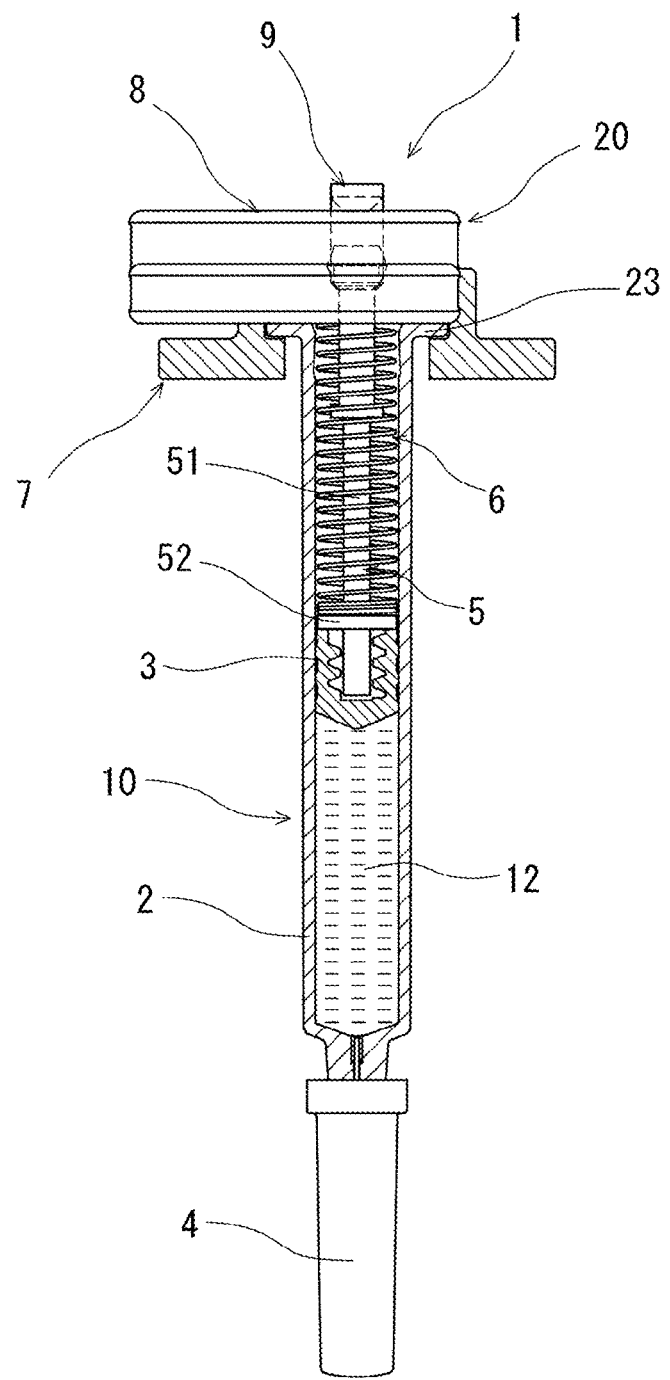
FIG. 8 is an explanatory view to describe the operation of the liquid medicine administration device illustrated in FIG. 1.
Figure 17:
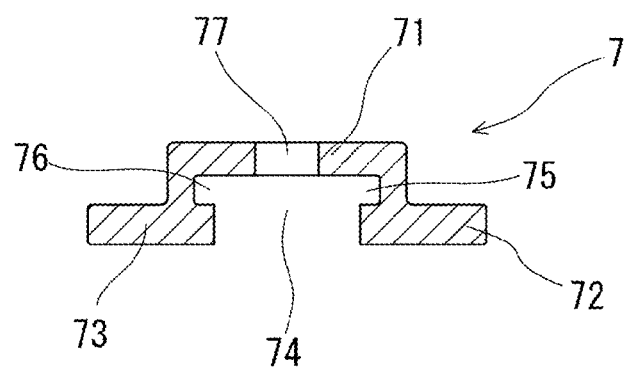
FIG. 17 is a longitudinal sectional view of the flange attachment member illustrated in FIG. 15.
Figure 18:
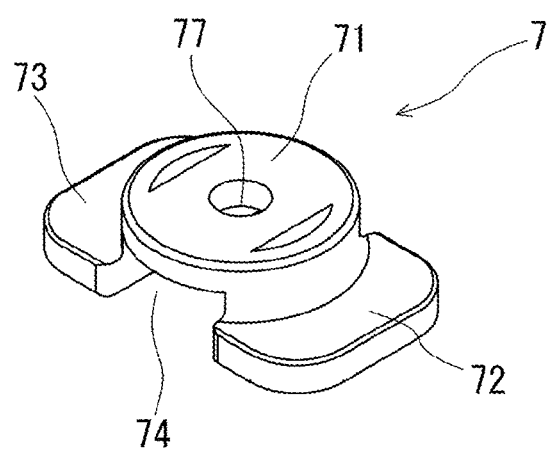
FIG. 18 is a perspective view of the flange attachment member illustrated in FIG. 15 in a view from above.
Figure 19:
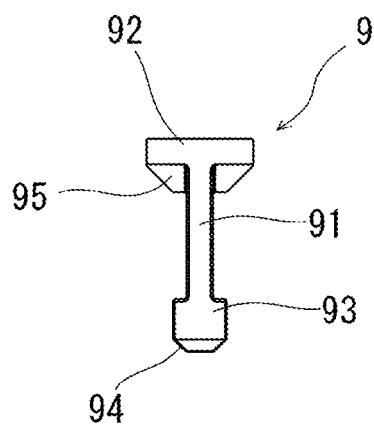
FIG. 19 is a front view of an operating member used in the liquid medicine administration device illustrated in FIG. 1.
Figure 20:
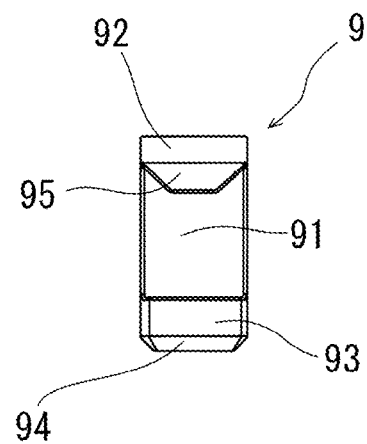
FIG. 20 is a left side view of an operation state holding member illustrated in FIG. 19.
Figure 21:
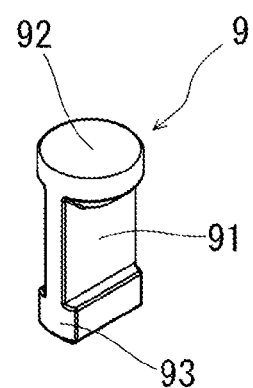
FIG. 21 is a perspective view of the operation state holding member illustrated in FIG. 19 in a view from above.

Additionally, as illustrated in FIGS. 8 and 17, flange housing portions 75 and 76 that house an outer peripheral portion of the flange 23 are provided between the attachment member body portion 71 and the respective flange gripping portions 72 and 73. When the flange attachment member 7 is attached to the flange 23 of the outer cylinder 2, a proximal end surface of the outer cylinder 2 inserted into the outer cylinder inserting portion 74 abuts on a distal end surface of the attachment member body portion 71, and also, the flange 23 of the outer cylinder 2 is housed in the flange housing portions 75 and 76 of the flange attachment member 7. Consequently, the flange 23 of the outer cylinder 2 is gripped by the flange gripping portions 72 and 73 and the attachment member body portion 71, and detachment of the flange attachment member 7 from the outer cylinder 2 is inhibited.

Additionally, as illustrated in FIG. 5, the gasket pressing member 5 and the biasing member 6 arranged in the compressed state between the gasket pressing member 5 and the flange attachment member 7 are housed inside the prefilled syringe 10.

Figure 12:
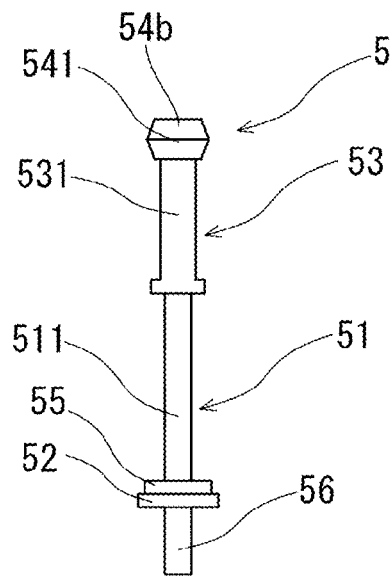
FIG. 12 is a front view of a gasket pressing member used in the liquid medicine administration device illustrated in FIG. 1.
Figure 13:
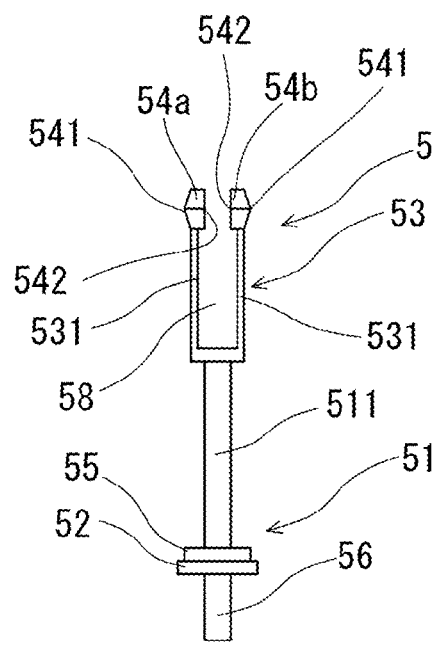
FIG. 13 is a left side view of the gasket pressing member illustrated in FIG. 12.
Figure 14:
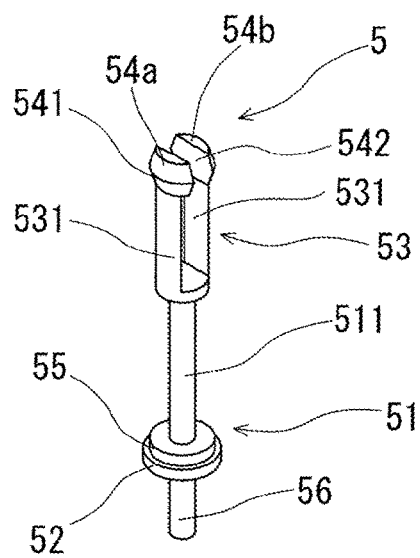
FIG. 14 is a perspective view of the gasket pressing member illustrated in FIG. 12 in a view from above.
Figure 15:
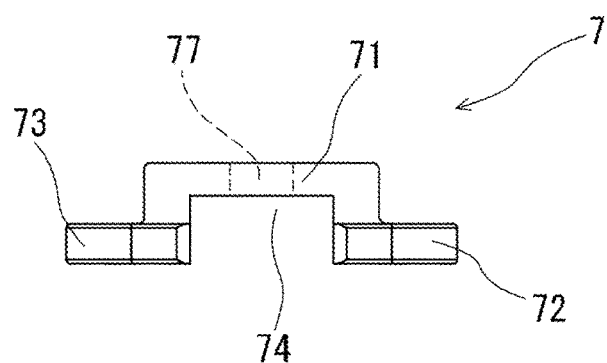
FIG. 15 is a front view of a flange attachment member used in the liquid medicine administration device illustrated in FIG. 1.
Figure 16:
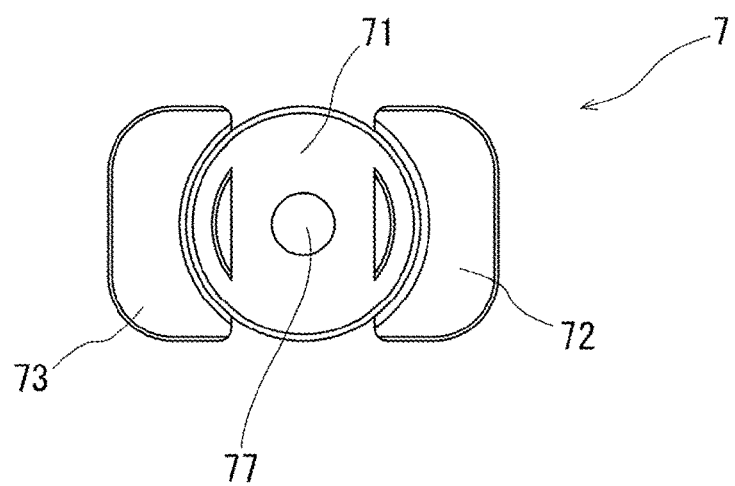
FIG. 16 is a plan view of the flange attachment member illustrated in FIG. 15.

Furthermore, in the liquid medicine administration device 1 of the present embodiment, as illustrated in FIGS. 12 to 14, the gasket pressing member 5 includes: the gasket pressing portion 51 having a distal end portion provided with the pressing body portion 52 capable of pressing the gasket 3 in the distal end direction; and the deformable portion 53 extending from the gasket pressing portion 51 in the proximal end direction. The deformable portion 53 includes: an engagement portion 541 provided at a proximal end portion of the deformable portion 53 and engaged with the attachment member body portion 71; and the abutment portion 542 provided at a position different from the engagement portion 541.

Additionally, in the present embodiment, the deformable portion 53 includes: a plurality of deformable body portions 531 that are deformable; an insertion space 58 formed between the plurality of deformable body portions 531 that are deformable; and a plurality of engagement portions 541 respectively provided at proximal end portions of the plurality of deformable body portions 531 and protruding laterally outward. Each of the plurality of deformable body portions 531 that are deformable includes: a counter surface facing the insertion space; and the abutment portion 542 provided on the counter surface. Additionally, the engagement holding portion 93 of the operating member 9 is inserted into the insertion space 58.

Furthermore, in the liquid medicine administration device 1 of the present embodiment, the deformable portion 53 includes: the two deformable body portions 531 facing each other and elastically deformable; and the insertion space 58 provided between the two deformable body portions 531. The two deformable body portions 531 include two bulges 54a and 54b provided at proximal end portions of the respective deformable body portions 531. Each of the two bulges 54a and 54b has an outer surface protruding outward and an inner surface protruding inward. The respective outer surfaces of the two bulges 54a and 54b constitute the two engagement portions 541, and the respective inner surfaces of the two bulges 54a and 54b constitute the abutment portions 542. In other words, each of the two bulges 54a and 54b includes: the engagement portion 541 protruding laterally outward; and the abutment portion 542 provided on the counter surface facing the insertion space 58. The abutment portion 542 protrudes toward the insertion space. Furthermore, the insertion space 58 provided in the deformable portion 53 (between the two deformable body portions 531) defines: the abutment positions where the engagement holding portion 93 of the operating member 9 abuts on the abutment portions 542; the separation positions that are located more on the distal end side than the abutment positions and are the positions where the engagement holding portion 93 is separated from the abutment portions 542. The deformable portion 53 of the gasket pressing member 5 is deformed by the two bulges 54a and 54b being pressed in a direction approaching to each other. Furthermore, a distance between the two bulges 54a and 54b is maintained and deformation of the deformable portion 53 is inhibited by the abutment between the engagement holding portion 93 of the operating member 9 and the abutment portions 542 of the gasket pressing member 5. Note that inner surfaces of the bulges 54a and 54b may not necessarily protrude inward. Additionally, the abutment portions 542 may be not necessarily located on the inner surfaces of the bulges 54a and 54b but may be located more on the distal end side than the inner surfaces are, and may be provided on the counter surfaces of the deformable body portions 531.

Furthermore, as illustrated in FIG. 5 and FIGS. 8 to 14, the gasket pressing portion 51 includes: the pressing body portion 52 provided at the distal end portion of the gasket pressing portion 51; a shaft portion 511 extending from a proximal end of the pressing body portion 52 in the proximal end direction; and a distal end protrusion 56 protruding from the pressing body portion 52 in the distal end direction.

Additionally, as illustrated in FIG. 5, the gasket pressing member 5 is substantially entirely housed inside the outer cylinder 2, and the proximal end portions (two bulges 54a and 54b) of the deformable portion provided with the above-described engagement portions 541 protrude from the through hole 77 of the flange attachment member body portion 71 of the flange attachment member 7 attached to the outer cylinder 2, and distal end portions of the engagement portions 541 are engaged with a proximal end outer edge portion of the through hole 77 of the flange attachment member body portion 71. Furthermore, the distal end protrusion 56 of the gasket pressing member 5 enters an internal space of the gasket 3, and the pressing body portion 52 abuts on a proximal end surface of the gasket 3. Additionally, the biasing member 6 is arranged and housed inside the outer cylinder in the compressed state between the gasket pressing member 5 and the flange attachment member 7. As the biasing member 6, a coil spring is preferably used.

In the present embodiment, a distal end portion 61 of the biasing member 6 houses a small-diameter portion 55 formed on the proximal end side of the pressing body portion 52 of the gasket pressing member 5, and a distal end of the distal end portion 61 abuts on a proximal end surface of the pressing body portion 52. Therefore, the distal end portion 61 of the biasing member 6 is in a stable state. Note that the distal end portion 61 of the biasing member 6 may be fixed to the above-described small-diameter portion 55. Additionally, a proximal end portion 62 of the biasing member 6 abuts on the distal end surface of the flange attachment member body portion 71 of the flange attachment member 7. Specifically, the proximal end portion 62 abuts on a part of the flange attachment member body portion 71 located in the vicinity of a distal end outer edge portion of the through hole 77.

Additionally, as illustrated in FIGS. 1 to 9, particularly in FIGS. 5 to 7 and FIG. 9, the liquid medicine administration device 1 includes the operating member 9 arranged in the manner displaceable with respect to the gasket pressing member 5. In the present embodiment, the operating member 9 includes: the operating portion 92; an extending portion 91 extending from the operating portion 92 in the distal end direction; and the engagement holding portion 93 extending from a distal end of the extending portion 91 in the distal end direction and laterally protruding more than the extending portion 91. Specifically, as illustrated in FIGS. 5 and 6, FIGS. 9 to 11, and FIGS. 19 to 21, the operating member 9 includes: the operating portion 92 having a disc shape; the extending portion 91 having a plate shape; the engagement holding portion 93 formed of a thick-walled portion continuous to the distal end of the extending portion 91; and a distal end tapered portion 94 extending from a distal end of the engagement holding portion 93 in the distal end direction and including an inclined surface inclined inward. The operating portion 92 is a flange portion protruding laterally more than the extending portion 91. Furthermore, in the present embodiment, the operating member 9 includes an operation engagement portion 95 arranged between the operating portion 92 and the extending portion 91 and protruding laterally more than the extending portion 91.

Furthermore, as illustrated in FIG. 5, the engagement holding portion 93 of the operating member 9 abuts on the abutment portions 542 of the deformable portion 53 of the gasket pressing member 5 to inhibit the deformation of the deformable portion 53. Specifically, the engagement holding portion 93 is inserted into the insertion space 58 of the deformable portion 53 of the gasket pressing member 5 and abuts on the abutment portion 53 to inhibit the deformation of the deformable portion 53. Consequently, the engagement between the engagement portions 541 of the deformable portion 53 and the attachment member body portion 71 of the flange attachment member 7 is maintained. Furthermore, in the present embodiment, both side surfaces of the engagement holding portion 93 of the operating member 9 abut on the two abutment portions 542 that are the respective inner surfaces of the two bulges 54a and 54b, and the two bulges 54a and 54b are inhibited from approaching to each other, and a distance between the outer surfaces of the two engagement portions 541 respectively provided at the two bulges 54a and 54b is maintained in a state larger than a diameter of the through hole 77. Note that the two bulges 54a and 54b may be slightly pushed and expanded by the engagement holding portion 93 of the operating member 9. Note that since the operating member 9 includes the distal end tapered portion 94 extending from the engagement holding portion 93 in the distal end direction and having the inclined surface inclined inward as described above, insertion work into the insertion space 58 (between the two bulges 54a and 54b) is facilitated.

Furthermore, the liquid medicine administration device 1 and the gasket biasing member assembly 20 of the present embodiment include the operation inhibiting member 8 that inhibits operation of the operating member 9 as illustrated in FIGS. 1 to 11 and FIGS. 22 to 24.

The operation inhibiting member 8 includes an inhibiting portion that inhibits the operation of the operating member 9 by being engaged with the operating member 9. Additionally, the operation inhibiting member 8 is displaceable with respect to the operating member 9 from an inhibiting position where the inhibiting portion is engaged with the operating member 9 to a releasing position where the engagement between the inhibiting portion and the operating member 9 is released. Furthermore, in the present embodiment, the operation inhibiting member 8 includes an insertion port 84 into which the extending portion 91 of the operating member 9 is inserted. The insertion port 84 includes: a first opening 84a having a width narrower than a width of the operation engagement portion 95; and a second opening 84b communicating with the first opening 84a and having a width wider than the width of the operation engagement portion 95. Additionally, when the operation inhibiting member 8 is located at the inhibiting position, an edge portion of the first opening 84a functions as the inhibiting portion by being engaged with the operation engagement portion 95 of the operating member 9. Furthermore, when the operation inhibiting member 8 is located at the releasing position, the operation engagement portion 95 of the operating member 9 is located at a position facing the second opening 84b, that is, on the second opening 84b, and the operating member 9 can be pushed in the distal end direction with respect to the gasket pressing member 5.

Figure 22:
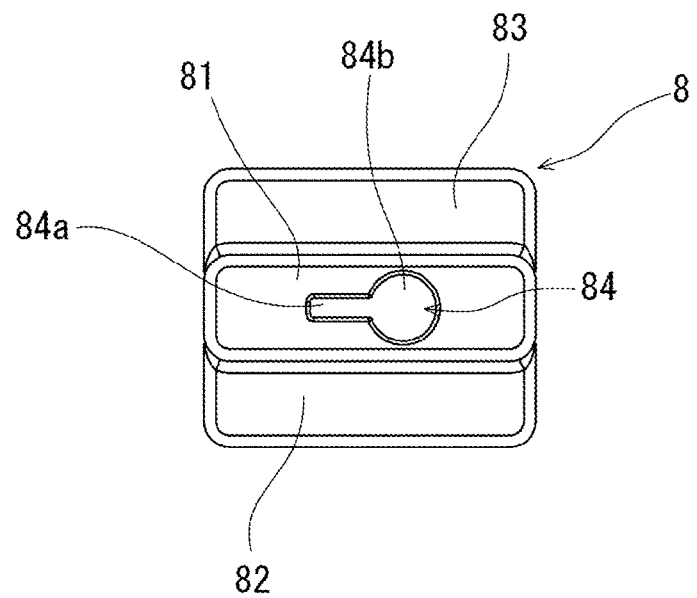
FIG. 22 is a plan view of an operation inhibiting member used in the liquid medicine administration device illustrated in FIG. 1.
Figure 23:
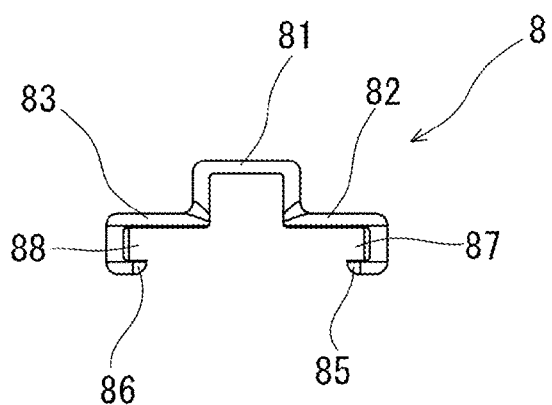
FIG. 23 is a left side view of the operation inhibiting member illustrated in FIG. 22.
Figure 24:
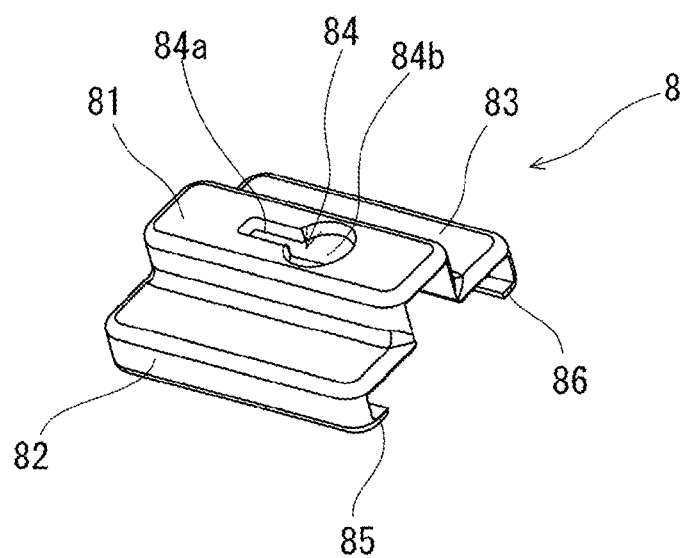
FIG. 24 is a perspective view of the operation inhibiting member illustrated in FIG. 22 in a view from above.

Specifically, as illustrated in FIGS. 22 to 24, the operation inhibiting member 8 includes a base portion 81 and two attachment portions 82 and 83 extending in the distal end direction from both side portions of the base portion 81. The attachment portions 82 and 83 include claw portions 85 and 86 provided at respective distal end portions and abutting on the distal end surface of the attachment member body portion 71 of the flange attachment member 7, and housing portions 87 and 88 that slidably house the side portions of the attachment member body portion 71 of the flange attachment member 7. Additionally, the base portion 81 includes the insertion port 84 passing through the base portion 81, and the extending portion 91 of the operating member 9 is inserted into the insertion port 84.

Figure 6:
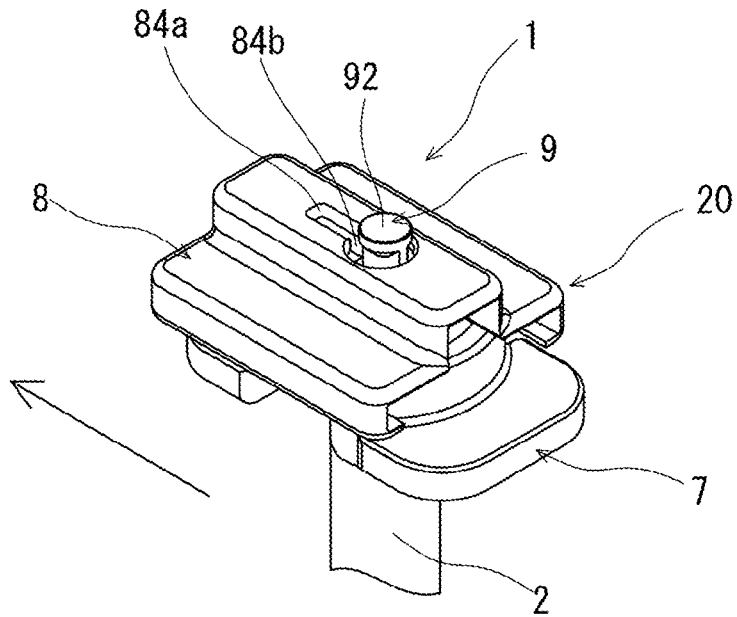
FIG. 6 is an explanatory view to describe operation of the liquid medicine administration device illustrated in FIG. 1.
Figure 7:
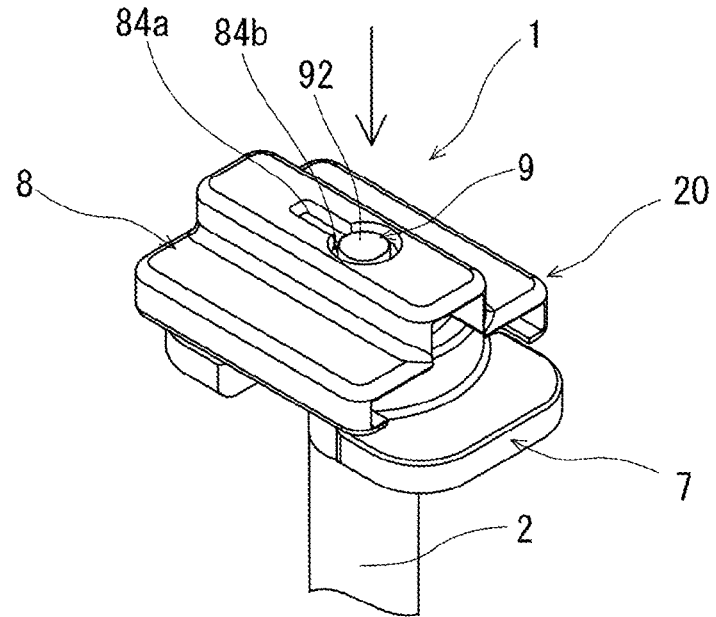
FIG. 7 is an explanatory view to describe the operation of the liquid medicine administration device illustrated in FIG. 1.

As illustrated in FIGS. 3, 4, 6, 7, 22, and 24, the insertion port 84 is a long port extending in a direction perpendicular to the extending direction of the extending portion 91 of the operating member 9. The insertion port 84 includes, on one end side in the extending direction thereof, a first opening (opening to inhibit operation) 84a having a narrow width and hindering entrance of the operating portion 92 of the operating member 9, and further includes, on the other end side in the extending direction of the insertion port 84, a second opening (opening to allow operation) 84b that allows the operating member 9 to be pushed in (entrance of the operating portion 92). More specifically, the first opening 84a is formed in a size such that: the extending portion 91 of the operating member 9 can pass through the first opening; and the operation engagement portion 95 and the operating portion 92 cannot enter the first opening. Additionally, the second opening 84b is formed larger than the engagement portion 95 and the operating portion 92 of the operating member 9, and as illustrated in FIG. 7, the engagement portion 95 and the operating portion 92 can enter the second opening 84b by pressing the operating portion 92 in the distal end direction.

Additionally, the operation inhibiting member 8 is attached to the flange attachment member 7 in a manner slidable in the extending direction of the insertion port 84. As illustrated in FIG. 6, the operation inhibiting member 8 is slid with respect to the operating member 9 by being pushed in an arrow direction. A place in the insertion port 84 where the operating member 9 passes through is changed by such sliding (displacement) of the operation inhibiting member 8 with respect to the operating member 9. When the operation inhibiting member 8 is located at the inhibiting position illustrated in FIG. 4, the extending portion 91 of the operating member 9 is inserted into the first opening 84*a*, and the edge portion of the first opening 84*a* is engaged with the operation engagement portion 95 of the operating member 9 and functions as the inhibiting portion. Additionally, when the operation inhibiting member 8 is displaced with respect to the operating member 9 from the inhibiting position to the releasing position illustrated in FIG. 6, the extending portion 91 of the operating member 9 is inserted into the first opening 84*a*, and the operation engagement portion 95 of the operating member 9 is located at a position facing the second opening 84*b*, that is, on the second opening 84*b*, and it becomes possible to push the operating member 9 in the distal end direction with respect to the gasket pressing member 5.

Next, an assembly process (manufacturing method) of the gasket biasing member assembly 20 according to an embodiment of the present invention will be described with reference to FIGS. 32 to 34.

First, the gasket pressing member 5, the biasing member (coil spring) 6, the flange attachment member 7, the operation inhibiting member 8, and the operating member 9 that are the constituent members of the gasket biasing member assembly 20 illustrated in FIG. 11 are prepared.

Next, the gasket biasing member assembly is assembled.

The operation inhibiting member 8 is slid from a side surface side of the flange attachment member 7, and the operation inhibiting member 8 is attached to the flange attachment member 7. In this initial attached state, the second opening 84*b* of the insertion port 84 of the operation inhibiting member 8 is aligned with the through hole 77 of the attachment member body portion 71 of the flange attachment member 7. Then, the gasket pressing member 5 is inserted into the biasing member 6 from the distal end side, and the distal end portion 61 of the biasing member 6 is attached to the pressing body portion 52. The proximal end portion 62 of the biasing member 6 is made to abut on the distal end surface of the attachment member body portion 71 of the flange attachment member 7, further the gasket pressing member 5 is moved in the proximal end direction with respect to the flange attachment member 7, and the deformable portion 53 of the gasket pressing member 5 is inserted into the through hole 77 of the flange attachment member 7. Then, the proximal end portion of the deformable portion 53 is made to protrude in the proximal end direction from the through hole 77, and the distal end portion of each engagement portion 541 of the deformable portion 53 is engaged with the proximal end outer edge portion of the through hole 77 of the attachment member body portion 71.

Then, the engagement holding portion 93 of the operating member 9 is inserted into the insertion space 58 of the deformable portion 53 of the gasket pressing member 5 through the second opening 84*b* of the insertion port 84 of the operation inhibiting member 8, and made to abut on the abutment portions 542. Then, the operation inhibiting member 8 is slid to displace the operation inhibiting member 8 with respect to the operating member 9 from the releasing position where the operation engagement portion 95 of the operating member 9 faces the second opening 84*b* to the inhibiting position where the operation engagement portion 95 of the operating member 9 is engaged with the edge portion of the first opening 84*a*. Consequently, the gasket biasing member assembly 20 of the embodiment illustrated in FIGS. 32 to 34 is assembled.

Figure 32:
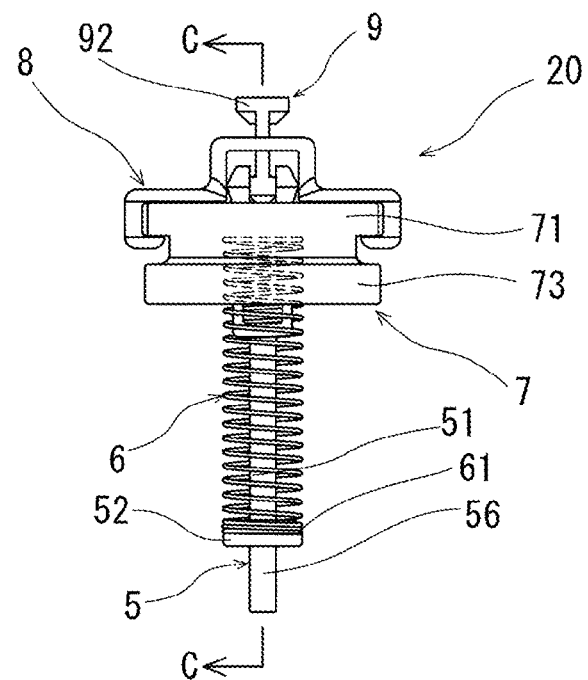
FIG. 32 is a left side view of a gasket biasing member assembly according to an embodiment of the present invention used in the liquid medicine administration device illustrated in FIG. 1.
Figure 34:
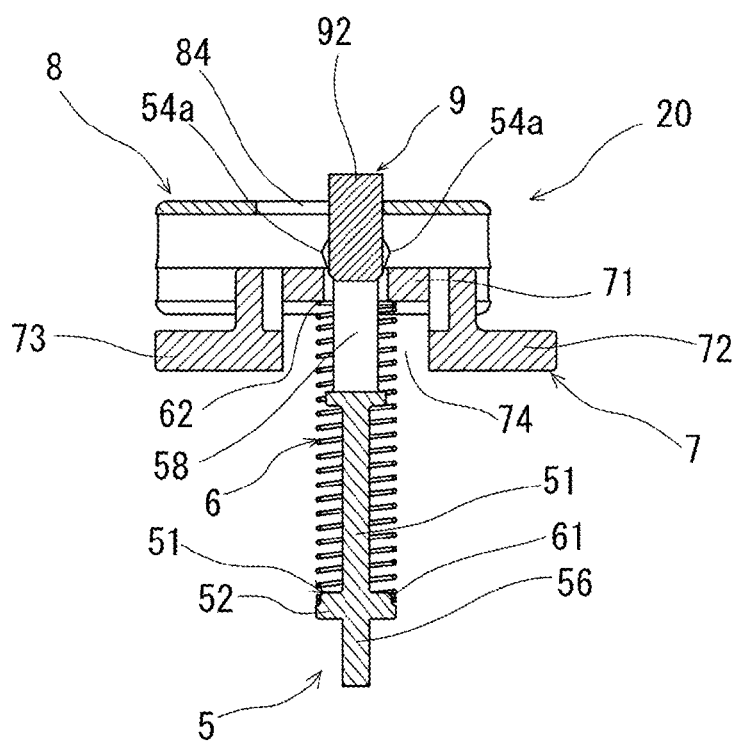
FIG. 34 is a cross-sectional view taken along a line C-C of FIG. 32.

In the gasket biasing member assembly 20, as illustrated in FIGS. 32 to 34, the biasing member 6 (coil spring) is arranged in the compressed state between the gasket pressing member 5 and the flange attachment member 7 by engagement between the engagement portion 541 of the deformable portion 53 and the attachment member body portion 71 of the flange attachment member 7. The engagement between the engagement portion 541 of the deformable portion 53 and the attachment member body portion 71 can be released by deformation of the deformable portion 53. Additionally, the engagement holding portion 93 of the operating member 9 is located at the abutment position to abut on the abutment portions 542 of the deformable portion 53, the deformation of the deformable portion 53 is inhibited, and the engagement between the engagement portion 541 of the deformable portion 53 and the attachment member body portion 71 is held. Furthermore, the operation inhibiting member 8 is located at the inhibiting position where the edge portion of the first opening 84*a* functioning as the inhibiting portion is engaged with the operation engagement portion 95 of the operating member 9, and the operation of the operating member 9 is inhibited. Therefore, in the gasket biasing member assembly 20, the biasing member 6 in the compressed state is excellently held between the gasket pressing member 5 and the flange attachment member 7.

Next, the assembly process of the medicine administration device 1 according to an embodiment of the present invention using the above-described gasket biasing member assembly 20 will be described with reference to FIGS. 35 to 37.

The prefilled syringe 10 is prepared. The prefilled syringe 10 (outer cylinder 2 having the needle) prepared here includes an annular flange 23 having two long extending portions 23*a* facing each other and two short extending portions 23*b* facing each other as illustrated in FIG. 31.

Figure 35:
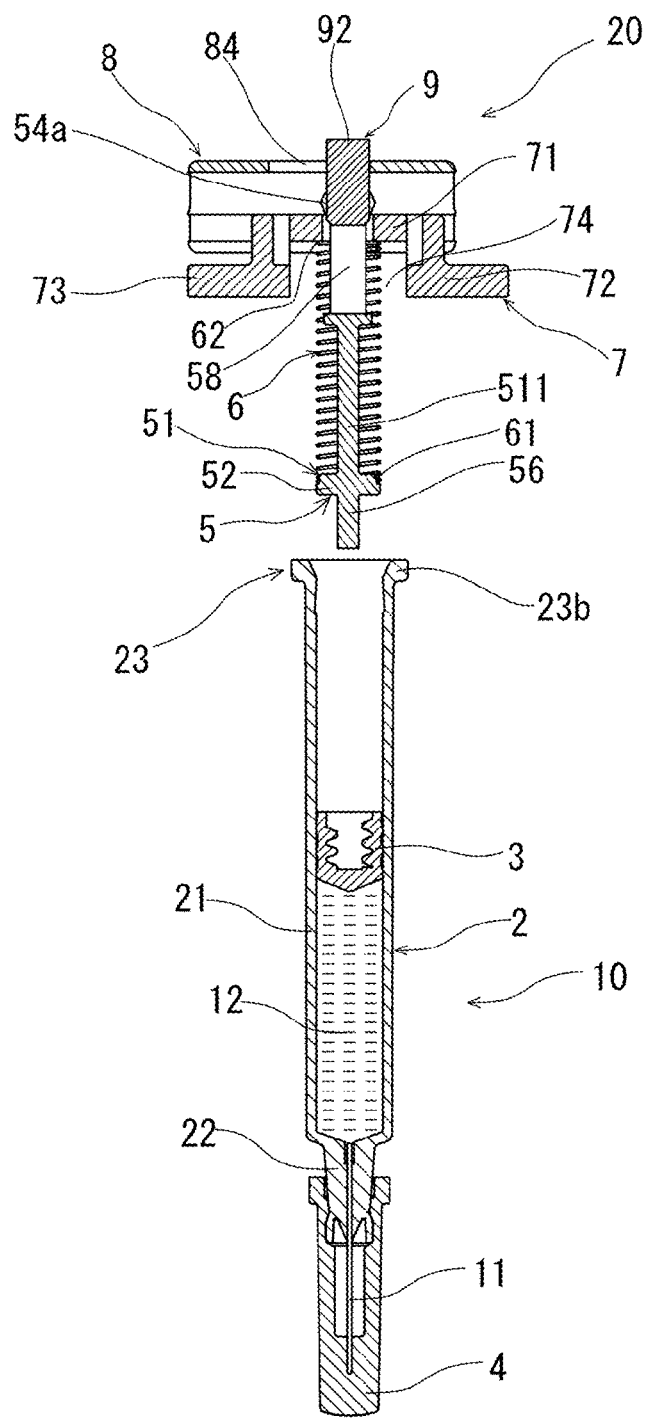
FIG. 35 is an explanatory view to describe an assembly process of the liquid medicine administration device illustrated in FIG. 1.
Figure 36:
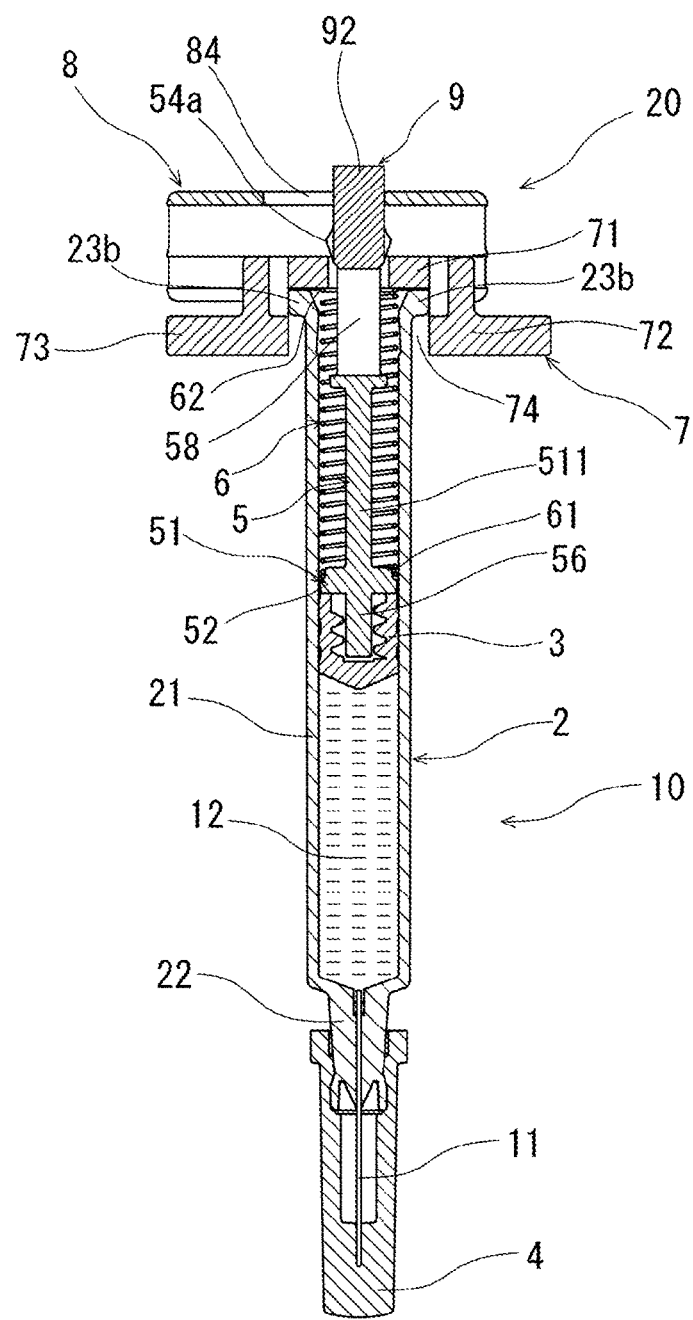
FIG. 36 is an explanatory view to describe the assembly process of the liquid medicine administration device illustrated in FIG. 1.
Figure 37:
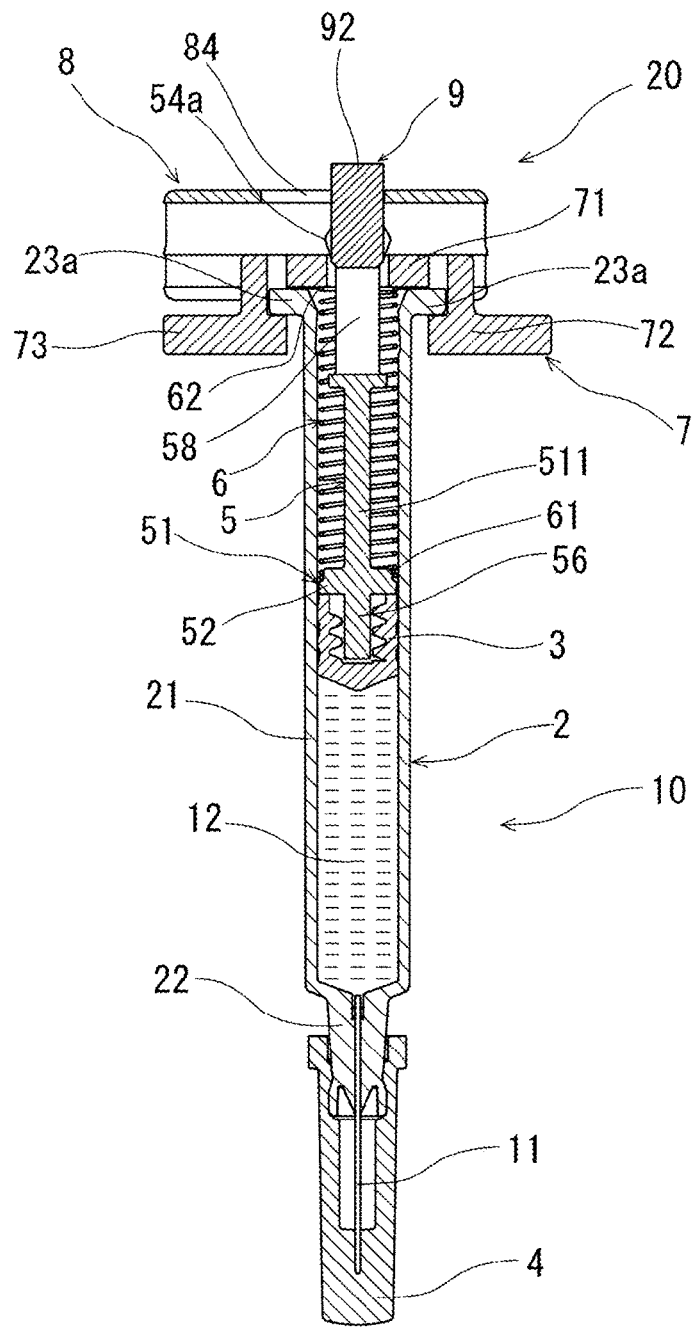
FIG. 37 is an explanatory view to describe the assembly process of the liquid medicine administration device illustrated in FIG. 1.

As illustrated in FIGS. 35 to 37, the prefilled syringe 10 is attached to the gasket biasing member assembly 20. In this attachment step, as illustrated in FIGS. 35 and 36, the gasket pressing member 5 and the biasing member 6 protruding in the distal end direction from the flange attachment member 7 are inserted into the outer cylinder 2 of the prefilled syringe 10, and the flange 23 of the prefilled syringe 10 is inserted into the outer cylinder inserting portion 74 of the flange attachment member 7.

Insertion of the flange 23 of the outer cylinder 2 into the outer cylinder inserting portion 74 of the flange attachment member 7 is performed by inserting the flange into the outer cylinder inserting portion 74 such that the short extending portions 23*b* facing each other of the flanges 23 face inner surfaces of the flange gripping portions 72 and 73 of the flange attachment member 7 respectively. A proximal end surface of the inserted prefilled syringe 10 (proximal end surface of the flange) abuts on the distal end surface of the attachment member body portion 71 of the flange attachment member 7.

Then, in this state, the gasket biasing member assembly 20 and the prefilled syringe 10 are relatively rotated. Specifically, the gasket biasing member assembly 20 is held and the prefilled syringe 10 is rotated around a central axis thereof. With this rotation, the two long extending portions 23*a* of the flange 23 of the prefilled syringe 10 enter the flange housing portions 75 and 76 of the flange attachment member 7 as illustrated in FIG. 37. Consequently, the prefilled syringe 10 is attached to the gasket biasing member assembly 20. Thus, the assembly of the liquid medicine administration device 1 of the embodiment illustrated in FIGS. 1 to 5 is completed. Furthermore, in the assembled liquid medicine administration device 1, the pressing body portion 52 of the gasket pressing member 5 is made to approach to or abut on the proximal end surface of the gasket 3, and the distal end protrusion 56 enters the internal space of the gasket 3.

Next, operation of the liquid medicine administration device 1 of the present embodiment will be described with reference to the drawings.

In the liquid medicine administration device 1 of the present embodiment, the states illustrated in FIGS. 1 to 5 are the initial states, in which the operating member 9 is located at the inhibiting position, the extending portion 91 of the operating member 9 is inserted into the first opening 84a, and the edge portion of the first opening 84a is engaged with the operation engagement portion 95 of the operating member 9. Therefore, the operating member 9 cannot be operated (cannot be pushed in the distal end direction). Also, in this state, as illustrated in FIG. 5, the engagement holding portion 93 of the operating member 9 abuts on the abutment portions 542 of the deformable portion 53 of the gasket pressing member 5 to inhibit the deformation of the deformable portion 53. Consequently, the engagement between the engagement portions 541 of the deformable portion 53 and the attachment member body portion 71 of the flange attachment member 7 is maintained, the biasing member 6 is held in the compressed state between the gasket pressing member 5 and the flange attachment member 7, and further the gasket pressing member 5 cannot be moved in the distal end direction with respect to the flange attachment member 7.

Additionally, as illustrated in FIG. 6, when the operation inhibiting member 8 is pushed in the arrow direction, the operation inhibiting member 8 is slid in the arrow direction, and the operation engagement portion 95 of the operating member 9 is located at the position facing the second opening 84b, that is, on the second opening 84b. Consequently, it becomes possible to push the operating member 9 in the distal end direction with respect to the gasket pressing member 5. Then, as illustrated in FIG. 7, the engagement portion 95 and the operating portion 92 enter the second opening 84b by pushing the operating portion 92 in the distal end direction. Furthermore, as illustrated in FIG. 9, since the engagement holding portion 93 of the operating member 9 is moved in the distal end direction, the engagement holding portion 93 is displaced from the abutment position to abut on the abutment portions 542 of the deformable portion 53 to the separation position to be separated from the abutment portions 542, and deformation of the deformable portion 53 is allowed.

Note that, as illustrated in FIG. 9, the extending portion 91 of the operating member 9 is located between the two abutment portions 542 of the gasket pressing member 5 in this state. At this time, since the extending portion 91 is more recessed inward than the engagement holding portion 93, the extending portion 91 does not hinder the deformation of the deformable portion 53 in the direction in which the two engagement portions 541 approach to each other. Additionally, as illustrated in FIG. 9, in this state, the engagement holding portion 93 of the operating member 9 is located at the separation position that is located more on the distal end side than a position between the two abutment portions 542 inside the insertion space 58 of the gasket pressing member 5. At this time, since the width of the insertion space 58 at the separation position is larger than the width between the two abutment portions 542, the engagement holding portion 93 located at the separation position does not hinder the deformation of the deformable portion 53 in the direction in which the two engagement portions 541 approach to each other.

Since the engagement holding portion 93 of the operating member 9 is located at the separation position to be separated from the abutment portion 542, the deformable portion 53 can be deformed. Therefore, the deformable portion 53 is deformed in the direction in which the two engagement portions 541 approach to each other by the biasing force of the biasing member 6 received by the gasket pressing member 5, and the engagement between the engagement portions 541 of the deformable portion 53 and the attachment member body portion 71 is released. Then, the engagement portions 541 of the deformable portion 53 pass through the through hole 77 of the flange attachment member 7, and as illustrated in FIG. 10, the biasing force of the biasing member 6 held between the gasket pressing member 5 and the flange attachment member 7 in the compressed state is released, and then the biasing member 6 presses the gasket pressing member 5 in the distal end direction. The gasket 3 is pressed by the gasket pressing member 5, made to slide inside the outer cylinder 2 in the distal end direction while discharging the liquid medicine 12, and abuts on the proximal end surface of the distal end portion of the outer cylinder 2, thereby stopping. Consequently, discharge of the liquid medicine is completed.

As described above, in the liquid medicine administration device 1 of the present embodiment, the engagement holding portion 93 is separated from the abutment portions 542 of the gasket pressing member 5, and the abutment between the engagement holding portion 93 and the abutment portions 542 is released by pushing the operating portion 92 of the operating member 9. Furthermore, in the liquid medicine administration device 1 of the present embodiment, the engagement holding portion 93 is separated from the abutment portions 542 of the gasket pressing member 5, and the abutment between the engagement holding portion 93 and the abutment portions 542 is released also by pulling out the operating member 9.

Next, a liquid medicine administration device 30 of an embodiment illustrated in FIGS. 25 to 29 will be described.

A medicine administration device 30 of the present embodiment includes a prefilled syringe 10 and a gasket biasing member assembly 20a.

The liquid medicine administration device 30 of the present embodiment releases abutment between an engagement holding portion 18 and the abutment portions 542 of the deformable portion 53 by pushing an operating member 15 in a distal end direction with respect to a gasket pressing member 5, and the operating member 15 includes an operation pressing portion 19 arranged at a distal end portion, and the gasket pressing member 5 includes a pressing target portion 59 arranged on a proximal end of a gasket pressing portion 51 and capable of abutting on the operation pressing portion 19. Additionally, when the operating member 15 is pushed in the distal end direction with respect to the gasket pressing member 5, the operation pressing portion 19 of the operating member 15 abuts on the pressing target portion 59, and the gasket pressing member 5 can be pressed in the distal end direction by the operating member 15.

A basic configuration of the liquid medicine administration device 30 of the present embodiment and a basic configuration of the liquid medicine administration device 1 described above, in other words, a basic configuration of the gasket biasing member assembly 20a and a basic configuration of the gasket biasing member assembly 20 described above are the same. A different point is that the liquid medicine administration device 30 (gasket biasing member assembly 20*a*) of the present embodiment does not include the operation inhibiting member 8 included in the above-described liquid medicine administration device 1 (gasket biasing member assembly 20) and the operating member 15 including the engagement holding portion 18 is used instead of the operating member 9. The operating member 15 in the present embodiment can also be referred to as a pressing auxiliary member. The same components are denoted by the same reference signs and are to be referred to the above description.

Figure 25:
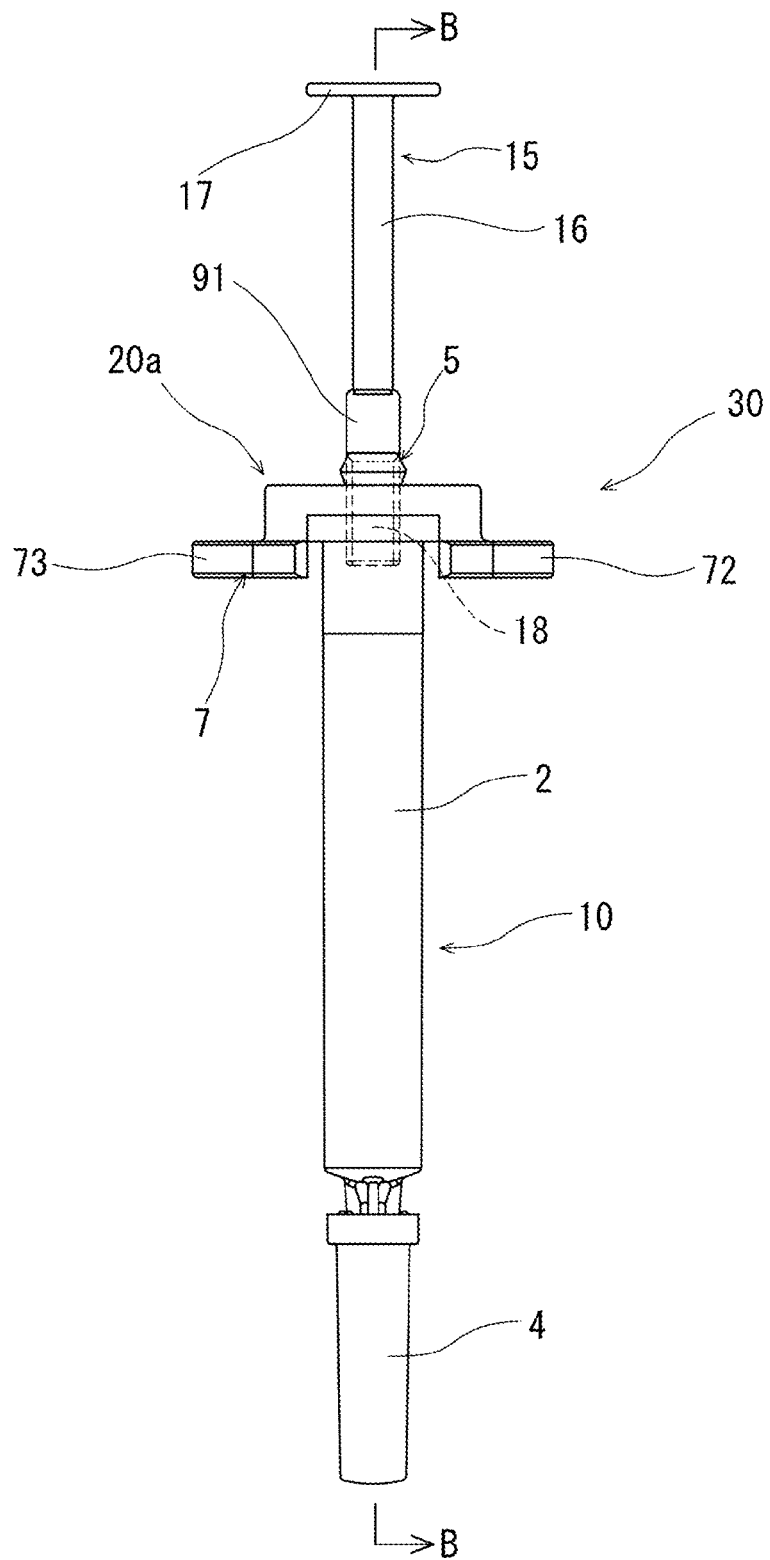
FIG. 25 is a front view of a liquid medicine administration device according to another embodiment of the present invention.
Figure 26:
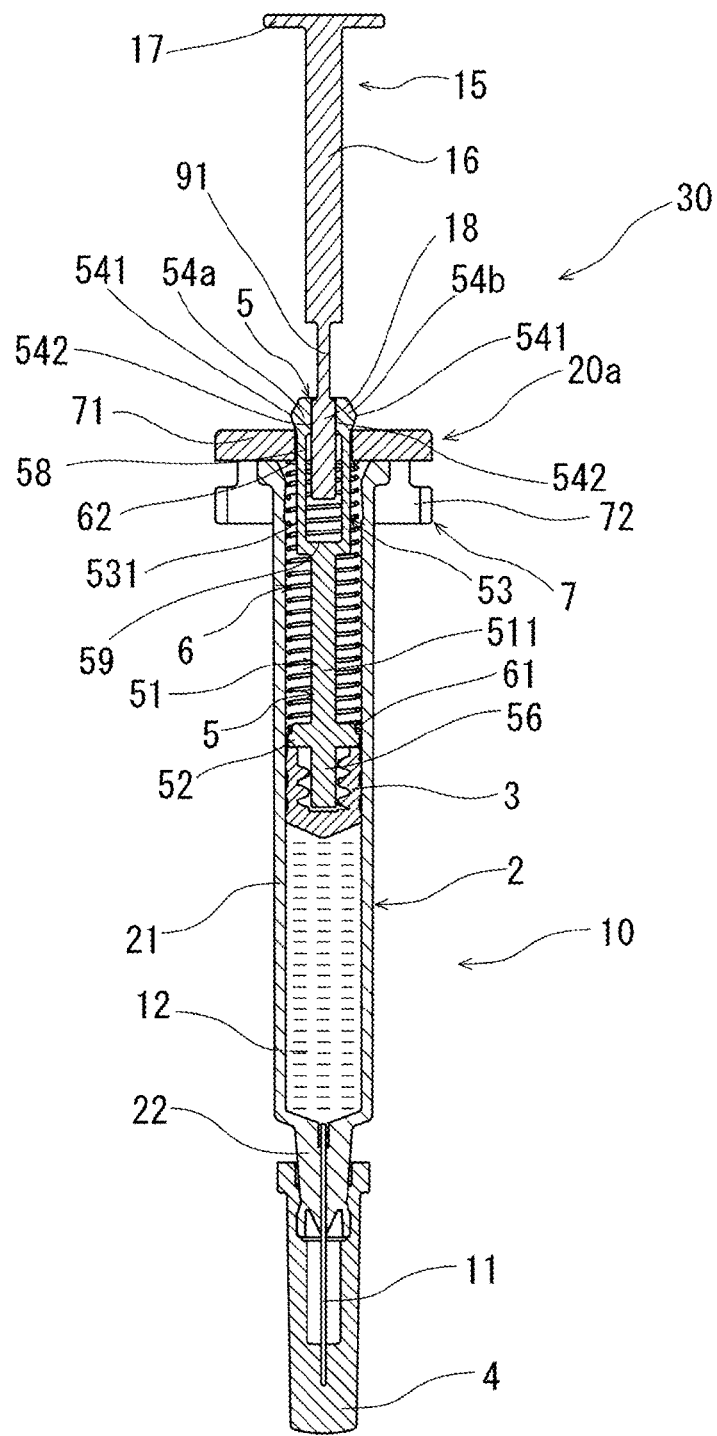
FIG. 26 is a cross-sectional view taken along a line B-B of FIG. 25.
Figure 27:
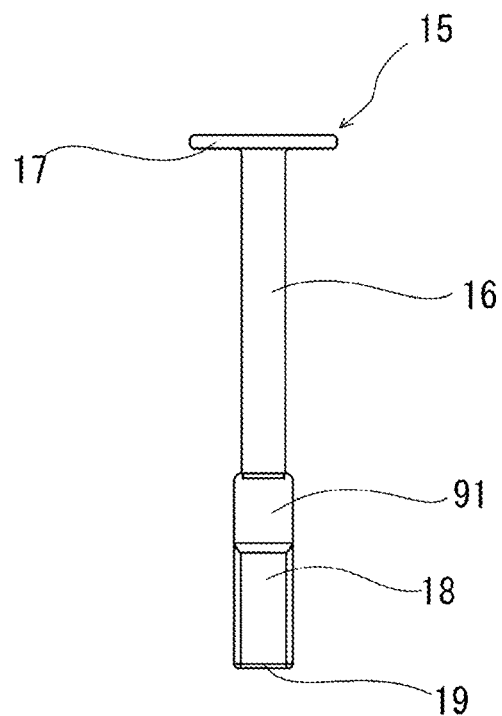
FIG. 27 is a front view of an operation state holding member used in the liquid medicine administration device illustrated in FIG. 25.
Figure 28:
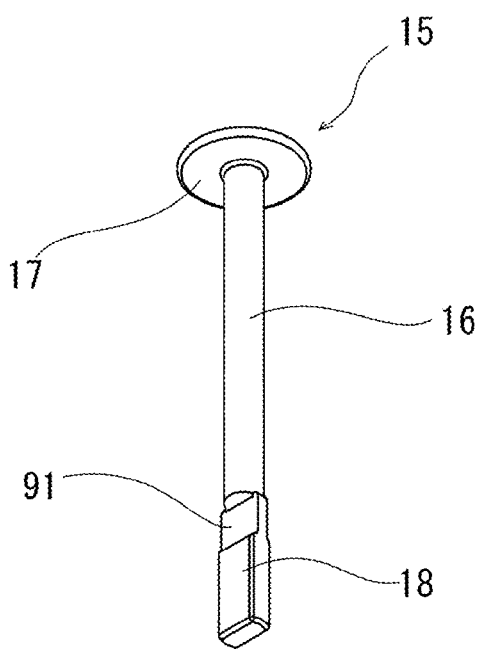
FIG. 28 is a perspective view of the operation state holding member of FIG. 27 in a view from below.

The prefilled syringe 10 is the same as one described above. A basic configuration of the gasket biasing member assembly is the same as the one described above. Since the liquid medicine administration device 30 of the present embodiment does not include the operation inhibiting member 8, engagement portions 541 of the gasket pressing member 5 engaged with a proximal end surface of a flange attachment member 7 and a proximal end outer edge portion of a through hole 77 of the flange attachment member 7 are exposed as illustrated in FIGS. 25 and 26. Additionally, the operating member 15 is inserted into a housing space 58 of the deformable portion 53 of the gasket pressing member 5.

As illustrated in FIGS. 25 to 29, the operating member 15 includes: a press operating portion 17; a shaft portion 16 extending from the press operating portion 17 in a distal end direction by a predetermined length; an extending portion 91 extending in a distal end direction from a distal end of the shaft portion 16; the engagement holding portion 18 extending in a distal end direction of a distal end of the extending portion 91 and protruding laterally more than the extending portion 91; and the operation pressing portion 19 provided on a distal end side of the engagement holding portion 18. Specifically, the disc-shaped press operating portion 17, the shaft portion 16 having a columnar shape, the extending portion having a plate shape, the engagement holding portion 93 formed of a thick-walled portion continuous to the distal end of the extending portion 91, and the operation pressing portion 19 provided at the distal end of the engagement holding portion 18 are provided. In the present embodiment, the operation pressing portion 19 is formed of a distal end surface of the operating member 15. Furthermore, the engagement holding portion 18 includes a tapered surface extending toward the operation pressing portion 19 and inclined inward. The tapered surface has a function similar to a function of the distal end tapered portion 94 of the operating member 9. Additionally, an operating portion of the operating member 15 includes the press operating portion 17 and the shaft portion 16.

Furthermore, as illustrated in FIG. 26, the engagement holding portion 18 of the operating member 15 abuts on the abutment portions 542 of the deformable portion 53 of the gasket pressing member 5 to inhibit deformation of the deformable portion 53. Specifically, the engagement holding portion 18 is inserted into the insertion space 58 of the deformable portion 53 of the gasket pressing member 5 and abuts on the abutment portions 542 to inhibit the deformation of the deformable portion 53. Consequently, the engagement between the engagement portions 541 of the deformable portion 53 and the attachment member body portion 71 of the flange attachment member 7 is maintained. Furthermore, in the present embodiment, both side surfaces of the engagement holding portion 18 of the operating member 15 abut on the two abutment portions 542 that are inner surfaces of respective two bulges 54*a* and 54*b*, the two bulges 54*a* and 54*b* are inhibited from approaching to each other, and a distance between outer surfaces of the two engagement portions 541 respectively provided at the two bulges 54*a* and 54*b* is maintained in a state larger than a diameter of the through hole 77.

In the liquid medicine administration device 30 of the present embodiment also, the engagement holding portion 18 of the operating member 15 is displaced from an abutment position to a separation position, and the abutment between the engagement holding portion 18 of the operating member 15 and the abutment portions 542 of the gasket pressing member 5 is released by pushing the operating member 15 in the distal end direction with respect to the gasket pressing member 5. Note that, in this state, the extending portion 91 of the operating member 15 is located between the engagement portions 541 of the gasket pressing member 5. At this time, since the extending portion 91 is more recessed inward than the engagement holding portion 18, the extending portion 91 does not hinder deformation of the deformable portion 53 in the direction in which the two engagement portions 541 approach to each other. Furthermore, in the liquid medicine administration device 30 of the present embodiment also, the engagement holding portion 18 is separated from the abutment portions 542 of the gasket pressing member 5 and the abutment between the engagement holding portion 18 and the abutment portion 542 can be released also by pulling out the operating member 15.

Figure 29:
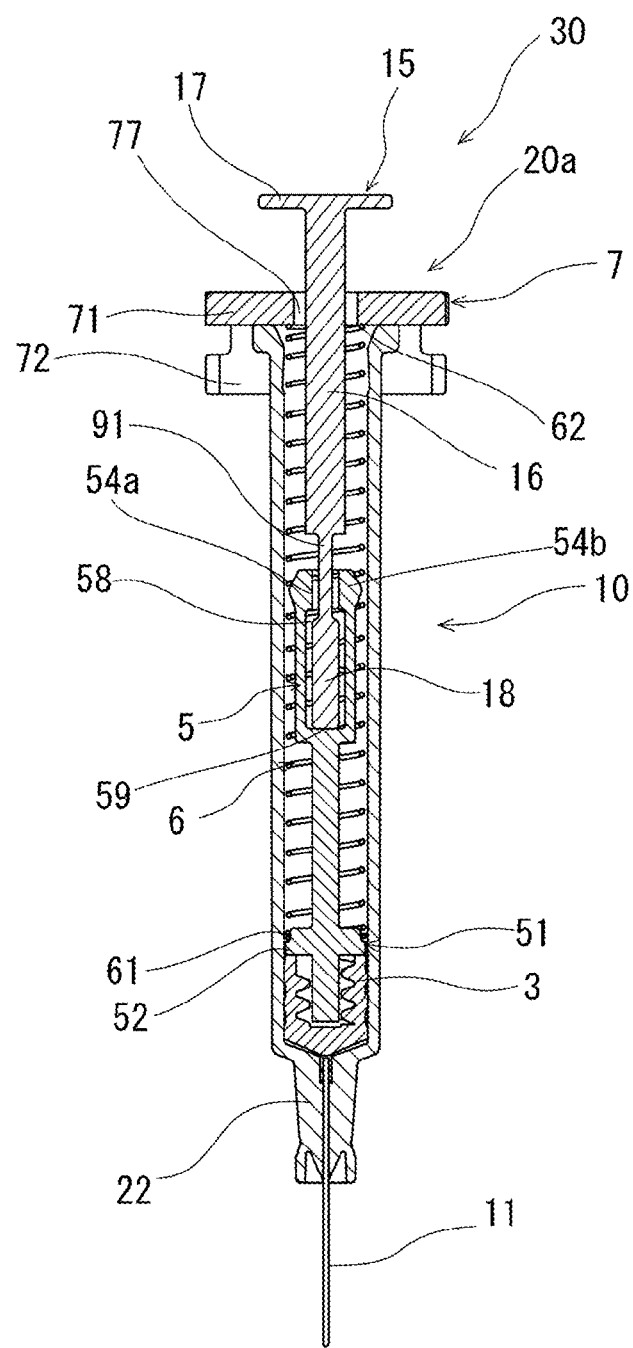
FIG. 29 is an explanatory view to describe operation of the liquid medicine administration device illustrated in FIG. 25.

Furthermore, in the liquid medicine administration device 30 of the present embodiment also, the deformable portion 53 can be deformed by the engagement holding portion 18 of the operating member 15 being located at the separation position to be separated from the abutment portions 542. Therefore, the deformable portion 53 is deformed in the direction in which the two engagement portions 541 approach to each other by biasing force of a biasing member 6 received by the gasket pressing member 5, and the engagement between the engagement portions 541 of the deformable portion 53 and the attachment member body portion 71 is released. Then, the engagement portions 541 of the deformable portion 53 pass through the through hole 77 of the flange attachment member 7, and as illustrated in FIG. 29, the biasing force of the biasing member 6 held between the gasket pressing member 5 and the flange attachment member 7 in a compressed state is released, and the biasing member 6 presses the gasket pressing member 5 in the distal end direction. The gasket 3 is pressed by the gasket pressing member 5, made to slide inside the outer cylinder 2 in the distal end direction while discharging the liquid medicine 12, and abuts on the proximal end surface of the distal end portion of the outer cylinder 2, thereby stopping. Consequently, discharge of the liquid medicine is completed.

Additionally, in the liquid medicine administration device 30 of the present embodiment, the operation pressing portion 19 of the operating member 15 abuts on the pressing target portion 59 provided at the proximal end portion of the gasket pressing portion 51 of the gasket pressing member 5 (the distal end portion of the deformable portion 53) by pushing the operating member 15, and the gasket pressing member 5 can be pressed by the operating member 15 in the distal end direction. Therefore, in a case where the gasket pressing member 5 is not smoothly moved only by pressing the gasket pressing member 5 in the distal end direction by the biasing force of the biasing member 6 or in a case where movement of the gasket pressing member 5 is slow because of high viscosity of the filled liquid medicine, the gasket pressing member and the gasket can be further pressed in the distal end direction by a user pressing the operating member 15 in the distal end direction. Since pressing in the distal end direction by the operating member 15 is assisted by the biasing member 6, the user can press the operating member 15 in the distal end direction with little force, in other words, can administer the liquid medicine.

Figure 30:
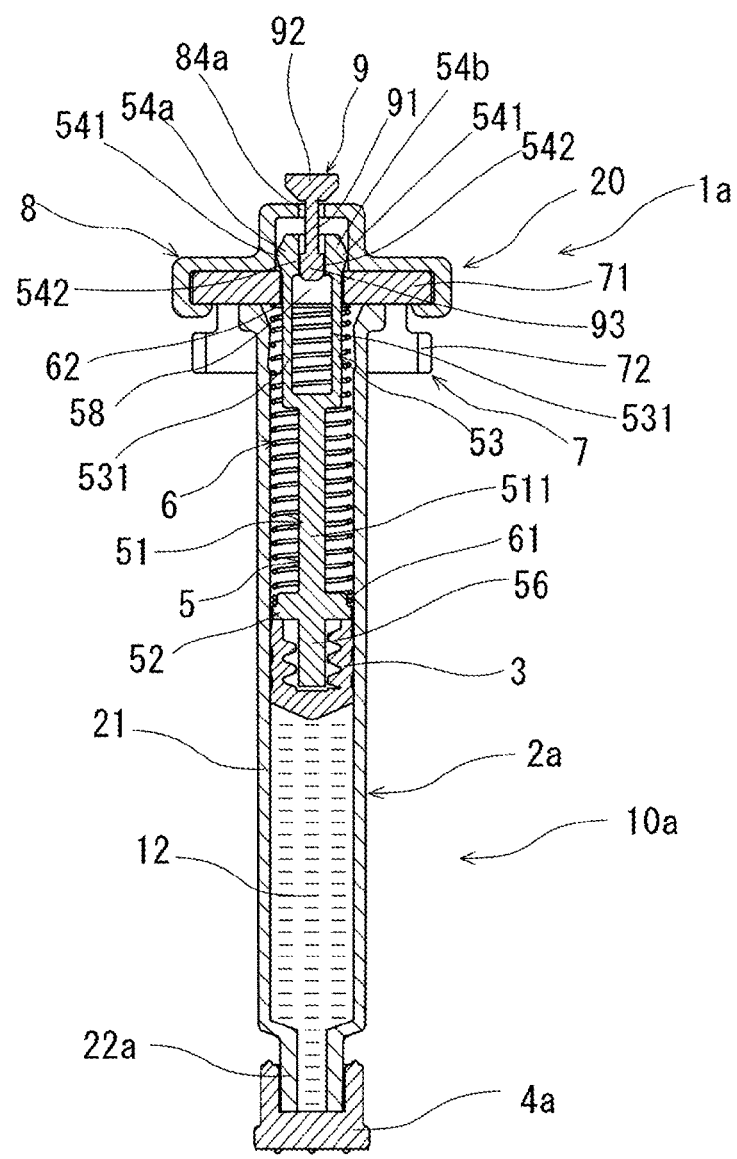
FIG. 30 is a cross-sectional view of a liquid medicine administration device according to still another embodiment of the present invention.

Furthermore, in all of embodiments described above, a prefilled syringe 10a including no injection needle may be used as a prefilled syringe, like a liquid medicine administration device 1a of an embodiment illustrated in FIG. 30.

The prefilled syringe 10a of the present embodiment includes: an outer cylinder 2a including a nozzle portion 22a having an open distal end; a sealing member (sealing cap) 4a that is detachably attached to the nozzle portion 22a and seals the open distal end; a gasket 3 slidably housed inside the outer cylinder 2a; and liquid medicine 12 filled inside the outer cylinder 2a. In the prefilled syringe 10a of the present embodiment, the nozzle portion 22a having the open distal end forms a liquid medicine discharge portion. Additionally, an injection needle hub can be attached to the nozzle portion 22a. Therefore, the cap 4a is detached and an injection needle is attached to the nozzle portion 22a during use. As illustrated in FIG. 30, the sealing member (sealing cap) 4a has a closed end, a cylindrical body portion, and a nozzle housing portion formed inside the cylindrical portion.

As a material forming the sealing member (sealing cap), it is preferable to use synthetic rubber such as natural rubber, isoprene rubber, butyl rubber, butadiene rubber, fluorine rubber, or silicone rubber, or an elastic material such as thermoplastic elastomer like olefinic elastomer or styrene elastomer.

INDUSTRIAL APPLICABILITY

The liquid medicine administration device according to an embodiment of the present invention is described below.

(1) A liquid medicine administration device including: a prefilled syringe that includes an outer cylinder, liquid medicine filled inside the outer cylinder, and a gasket slidably housed inside the outer cylinder; and a biasing member assembly that biases the gasket in a distal end direction in order to discharge the liquid medicine, in which the outer cylinder includes: a liquid medicine discharge portion provided at a distal end portion of the outer cylinder; and a flange provided at a proximal end portion of the outer cylinder, the biasing member assembly includes: a gasket pressing member capable of pressing the gasket in the distal end direction; a flange attachment member attached to the flange of the outer cylinder; a biasing member to bias the gasket pressing member in the distal end direction with respect to the flange attachment member; and an operating member arranged in a manner displaceable with respect to the gasket pressing member, the gasket pressing member includes: a gasket pressing portion having, in a distal end portion, a pressing body portion capable of pressing the gasket in the distal end direction; and a deformable portion extending from the gasket pressing portion in a proximal end direction, the flange attachment member includes an attachment member body portion having a through hole into which the deformable portion is inserted, the deformable portion includes: an engagement portion arranged at a proximal end portion of the deformable portion and engaged with the attachment member body portion; and an abutment portion arranged at a position different from the engagement portion and capable of abutting on the operating member, and the biasing member is arranged in a compressed state between the gasket pressing member and the flange attachment member by engagement between the engagement portion of the deformable portion and the attachment member body portion of the flange attachment member, the engagement between the engagement portion of the deformable portion and the attachment member body portion can be released by deformation of the deformable portion, and the operating member includes: an engagement holding portion that is displaceable from an abutment position to abut on the abutment portion of the deformable portion to a separation position to be separated from the abutment portion; and an operating portion to displace the operating member with respect to the gasket pressing member such that the engagement holding portion is displaced from the abutment position to the separation position, the deformation of the deformable portion is inhibited by abutment between the engagement holding portion located at the abutment position and the abutment portion of the deformable portion, and the engagement between the engagement portion of the deformable portion and the attachment member body portion is held, and the deformation of the deformable portion is allowed by displacing the engagement holding portion from the abutment position to the separation position by operating the operating portion, and the deformable portion is deformed and the engagement between the engagement portion of the deformable portion and the attachment member body portion is released by biasing force of the biasing member received by the gasket pressing member.

In this liquid medicine administration device, the engagement between the engagement portion of the gasket pressing member and the attachment member body portion is held by the engagement holding portion of the operating member abutting on the abutment portion of the gasket pressing member to inhibit the deformation of the deformable portion of the gasket pressing member, and therefore, it is possible to surely prevent biasing by the biasing member from being released until use. During the use, because the deformation of the deformable portion is allowed by operating the operating portion and separating the engagement holding portion of the operating member from the abutment portion of the gasket pressing member, the engagement between the engagement portion of the deformable portion and the attachment member body portion can be easily released. Therefore, discharging operation of the liquid medicine or assistance thereto can be facilitated.

Additionally, the above embodiments may also be those described below.

(2) The liquid medicine administration device recited in (1) above, in which the engagement holding portion is displaced from the abutment position to the separation position by pushing the operating member in the distal end direction with respect to the gasket pressing member, and the abutment between the engagement holding portion and the abutment portion of the deformable portion is released.

(3) The liquid medicine administration device recited in (1) or (2) above, in which the operating member includes: an extending portion extending in the distal end direction from the operating portion; and the engagement holding portion extending in the distal end direction from a distal end of the extending portion and protruding laterally more than the extending portion.

(4) The liquid medicine administration device recited in any one of (1) to (3) above, in which the deformable portion includes: a plurality of deformable body portions extending in a proximal end direction from the gasket pressing portion; an insertion space formed between the plurality of deformable body portions; and a plurality of the engagement portions provided at respective proximal end portions of the plurality of deformable body portions and protruding laterally outward, each of the plurality of deformable body portions that are deformable includes: a counter surface facing the insertion space; and the abutment portion provided on the counter surface, and the engagement holding portion of the operating member is inserted into the insertion space and abuts on the abutment portion.

(5) The liquid medicine administration device recited in any one of (1) to (4) above, in which the operating member is moved together with the gasket pressing member when the gasket pressing member is moved by the biasing force of the biasing member in the distal end direction with respect to the flange attachment member.

(6) The liquid medicine administration device recited in any one of (1) to (4) above, in which the abutment between the engagement holding portion and the abutment portion of the deformable portion is released by pushing the operating member in the distal end direction with respect to the gasket pressing member, the operating member includes an operation pressing portion arranged at a distal end portion of the operating portion, the gasket pressing member includes a pressing target portion arranged at a proximal end of the gasket pressing portion and capable of abutting on the operation pressing portion, and when the operating member is pushed in the distal end direction with respect to the gasket pressing member, the operation pressing portion abuts on the pressing target portion, and the gasket pressing member can be pressed in the distal end direction by the operating member.

(7) The liquid medicine administration device recited in any one of (1) to (6) above, in which the biasing member assembly includes an operation inhibiting member including an inhibiting portion that inhibits operation of the operating member by being engaged with the operating member, and the operation inhibiting member is displaceable with respect to the operating member from an inhibiting position where the inhibiting portion is engaged with the operating member to a releasing position where the engagement between the inhibiting portion and the operating member is released.

(8) The liquid medicine administration device recited in (7) above, in which the abutment between the engagement holding portion and the abutment portion of the deformable portion is released by pushing the operating member in the distal end direction with respect to the gasket pressing member, the operating member includes: an extending portion extending from the operating portion in the distal end direction; and an operation engagement portion arranged between the operating portion and the extending portion and protruding laterally more than the extending portion;

the operation inhibiting member includes an insertion port into which the extending portion of the operating member is inserted, the insertion port includes: a first opening having a width smaller than a width of the operation engagement portion; and a second opening communicating with the first opening and having a width larger than the width of the operation engagement portion, when the operation inhibiting member is located at the inhibiting position, the extending portion of the operating member is inserted into the first opening, and an edge portion of the first opening is engaged with the operation engagement portion and functions as the inhibiting portion, and when the operation inhibiting member is located at the releasing position, the extending portion of the operating member is inserted into the second opening, and the engagement portion is located at a position facing the second opening, and the operating member can be pushed in the distal end direction with respect to the gasket pressing member.

The gasket biasing member assembly according to an embodiment of the present invention is described below.

(9) A gasket biasing member assembly that biases a gasket of a syringe in a distal end direction in order to move the gasket in the distal end direction, the syringe including: an outer cylinder having a flange at a proximal end portion; and the gasket slidably housed inside the outer cylinder, in which the biasing member assembly includes: a gasket pressing member capable of pressing the gasket in the distal end direction, a flange attachment member attached to the flange of the outer cylinder; a biasing member to bias the gasket pressing member in the distal end direction with respect to the flange attachment member; and an operating member arranged in a manner displaceable with respect to the gasket pressing member, the gasket pressing member includes: a gasket pressing portion having, in a distal end portion, a pressing body portion capable of pressing the gasket in the distal end direction; and a deformable portion extending from the gasket pressing portion in a proximal end direction, the flange attachment member includes an attachment member body portion having a through hole into which the deformable portion is inserted, the deformable portion includes: an engagement portion arranged at a proximal end portion of the deformable portion and engaged with the attachment member body portion; and an abutment portion arranged at a position different from the engagement portion, and the biasing member is arranged in a compressed state between the gasket pressing member and the flange attachment member by engagement between the engagement portion of the deformable portion and the attachment member body portion of the flange attachment member, the engagement between the engagement portion of the deformable portion and the attachment member body portion can be released by deformation of the deformable portion, and the operating member includes: an engagement holding portion that is displaceable from an abutment position to abut on the abutment portion of the deformable portion to a separation position to be separated from the abutment portion; and an operating portion to displace the operating member with respect to the gasket pressing member such that the engagement holding portion is displaced from the abutment position to the separation position, the deformation of the deformable portion is inhibited by abutment between the engagement holding portion located at the abutment position and the abutment portion of the deformable portion, and the engagement between the engagement portion of the deformable portion and the attachment member body portion is held, and the deformation of the deformable portion is allowed by displacing the engagement holding portion from the abutment position to the separation position by operating the operating portion, and the deformable portion is deformed and the engagement between the engagement portion of the deformable portion and the attachment member body portion is released by biasing force of the biasing member received by the gasket pressing member.

In this gasket biasing member assembly, since the engagement holding portion of the operating member abuts on the abutment portion of the gasket pressing member to inhibit the deformation of the deformable portion of the gasket pressing member, the engagement between the engagement portion of the gasket pressing member and the attachment member body portion is held, and therefore, it is possible to surely prevent biasing by the biasing member from being released until use. During the use, since the deformation of the deformable portion is allowed by operating the operating portion and separating the engagement holding portion of the operating member from the abutment portion of the gasket pressing member, the engagement between the engagement portion of the deformable portion and the attachment member body portion can be easily released. Therefore, moving operation of the gasket and assistance thereto can be facilitated.

Additionally, the above embodiments may also be those described below.

(10) The gasket biasing member assembly recited in (9) above, in which the abutment between the engagement holding portion and the abutment portion of the deformable portion is released by pushing the operating member in the distal end direction with respect to the gasket pressing member.

(11) The gasket biasing member assembly recited in (9) or (10) above, in which the operating member includes: an extending portion extending in the distal end direction from the operating portion; and the engagement holding portion extending in the distal end direction from a distal end of the extending portion and protruding laterally more than the extending portion.

(12) The gasket biasing member assembly recited in any one of (9) to (11) above, in which the deformable portion includes: a plurality of deformable body portions that are deformable; an insertion space formed between the plurality of deformable body portions that are deformable; and a plurality of the engagement portions provided at respective proximal end portions of the plurality of deformable body portions and protruding laterally, each of the plurality of deformable body portions that are deformable includes: a counter surface facing the insertion space; and the abutment portion provided on the counter surface, and the engagement holding portion of the operating member is inserted into the insertion space.

(13) The gasket biasing member assembly recited in any one of (9) to (12) above, in which
the biasing member assembly includes an operation inhibiting member including an inhibiting portion that inhibits operation of the operating member by being engaged with the operating member, and
the operation inhibiting member is displaceable with respect to the operating member from an inhibiting position where the inhibiting portion is engaged with the operating member to a releasing position where the engagement between the inhibiting portion and the operating member is released.

The invention claimed is:
1. A liquid medicine administration device comprising:
a prefilled syringe comprising:
an outer cylinder,
liquid medicine filled inside the outer cylinder, and
a gasket slidably housed inside the outer cylinder; and
a biasing member assembly configured to bias the gasket in a distal end direction in order to discharge the liquid medicine;
wherein the outer cylinder comprises:
a liquid medicine discharge portion located at a distal end portion of the outer cylinder, and
a flange located at a proximal end portion of the outer cylinder;
wherein the biasing member assembly comprises:
a gasket pressing member configured to press the gasket in the distal end direction,
a flange attachment member attached to the flange of the outer cylinder,
a biasing member configured to bias the gasket pressing member in the distal end direction with respect to the flange attachment member, and
an operating member arranged displaceably with respect to the gasket pressing member;
wherein the gasket pressing member comprises:
a gasket pressing portion comprising, in a distal end portion, a pressing body portion capable of pressing the gasket in the distal end direction,
a deformable portion extending from the gasket pressing portion in a proximal end direction, and
a pressing target portion arranged at a proximal end of the gasket pressing portion,
wherein the flange attachment member comprises an attachment member body portion having a through hole into which the deformable portion is inserted;
wherein the deformable portion comprises:
an engagement portion arranged at a proximal end portion of the deformable portion and engaged with the attachment member body portion, and
an abutment portion arranged at a position different from the engagement portion and configured to abut on the operating member;
wherein the biasing member is arranged in a compressed state between the gasket pressing member and the flange attachment member by engagement between the engagement portion of the deformable portion and the attachment member body portion of the flange attachment member;
wherein the engagement between the engagement portion of the deformable portion and the attachment member body portion is releasable by deformation of the deformable portion; and
wherein the operating member comprises:
an engagement holding portion that is displaceable from (i) an abutment position at which the engagement holding portion abuts on the abutment portion of the deformable portion to (ii) a separation position at which the engagement holding portion is separated from the abutment portion of the deformable portion,
an operating portion configured to displace the operating member with respect to the gasket pressing member such that the engagement holding portion is displaced from the abutment position to the separation position, and
an operation pressing portion arranged at a distal end portion of the operating portion,
wherein the abutment between the engagement holding portion and the abutment portion of the deformable portion is releasable by pushing the operating member in the distal end direction with respect to the gasket pressing member, and wherein the pressing target portion is configured to abut on the operation pressing portion;

wherein, when the operating member is pushed in the distal end direction with respect to the gasket pressing member, the operation pressing portion abuts on the pressing target portion, and the gasket pressing member is pressable in the distal end direction by the operating member;

wherein, when the engagement holding portion is located at the abutment position, the deformation of the deformable portion is inhibited by abutment between the engagement holding portion and the abutment portion of the deformable portion, and the engagement between the engagement portion of the deformable portion and the attachment member body portion is held; and wherein, when the engagement holding portion is displaced from the abutment position to the separation position by operating the operating portion, the deformation of the deformable portion is allowed by displacing the engagement holding portion from the abutment position to the separation position, the deformable portion is deformed, and the engagement between the engagement portion of the deformable portion and the attachment member body portion is released by biasing force of the biasing member received by the gasket pressing member.

2. The liquid medicine administration device according to claim 1,
wherein the engagement holding portion is configured to be displaced from the abutment position to the separation position by pushing the operating member in the distal end direction with respect to the gasket pressing member.

3. The liquid medicine administration device according to claim 1,
wherein the operating member comprises:
an extending portion extending in the distal end direction from the operating portion, and
the engagement holding portion extending in the distal end direction from a distal end of the extending portion and protruding laterally more than the extending portion.

4. The liquid medicine administration device according to claim 1,
wherein the deformable portion comprises:
a plurality of deformable body portions extending in a proximal end direction from the gasket pressing portion,
an insertion space formed between the plurality of deformable body portions, and
a plurality of the engagement portions provided at respective proximal end portions of the plurality of deformable body portions and protruding laterally outward;
wherein each of the plurality of deformable body portions comprises:
a counter surface facing the insertion space, and
the abutment portion provided on the counter surface; and
wherein the engagement holding portion of the operating member is inserted into the insertion space and abuts on the abutment portion in the abutment position.

5. The liquid medicine administration device according to claim 1,
wherein, when the gasket pressing member is moved by the biasing force of the biasing member in the distal end direction with respect to the flange attachment member, the operating member is moved together with the gasket pressing member.

6. The liquid medicine administration device according to claim 1,
wherein the biasing member assembly comprises an operation inhibiting member comprising an inhibiting portion configured to inhibit operation of the operating member by being engaged with the operating member; and
wherein the operation inhibiting member is displaceable with respect to the operating member from (i) an inhibiting position at which the inhibiting portion is engaged with the operating member to (ii) a releasing position at which engagement between the inhibiting portion and the operating member is released.

7. The liquid medicine administration device according to claim 6,
wherein the abutment between the engagement holding portion and the abutment portion of the deformable portion is releasable by pushing the operating member in the distal end direction with respect to the gasket pressing member;
wherein the operating member comprises:
an extending portion extending from the operating portion in the distal end direction, and
an operation engagement portion arranged between the operating portion and the extending portion and protruding laterally more than the extending portion;
wherein the operation inhibiting member includes an insertion port into which the extending portion of the operating member is inserted;
wherein the insertion port comprises:
a first opening having a width smaller than a width of the operation engagement portion, and
a second opening communicating with the first opening and having a width larger than the width of the operation engagement portion;
wherein, when the operation inhibiting member is located at the inhibiting position, the extending portion of the operating member is inserted into the first opening, and an edge portion of the first opening is engaged with the operation engagement portion and functions as the inhibiting portion; and
wherein, when the operation inhibiting member is located at the releasing position, the extending portion of the operating member is inserted into the second opening, the engagement portion is located at a position facing the second opening, and the operating member is pushable in the distal end direction with respect to the gasket pressing member.

8. A gasket biasing member assembly configured to bias a gasket of a syringe in a distal end direction in order to move the gasket in the distal end direction, the syringe comprising an outer cylinder having a flange at a proximal end portion, and the gasket slidably housed inside the outer cylinder, the gasket biasing member assembly comprising:
a gasket pressing member configured to press the gasket in the distal end direction;
a flange attachment member configured to be attached to the flange of the outer cylinder;
a biasing member configured to bias the gasket pressing member in the distal end direction with respect to the flange attachment member;
an operating member arranged in a manner displaceable with respect to the gasket pressing member; and an operation inhibiting member comprising an inhibiting portion configured to inhibit operation of the operating member by being engaged with the operating member;

wherein the gasket pressing member comprises:
- a gasket pressing portion comprising, in a distal end portion, a pressing body portion configured to press the gasket in the distal end direction, and
- a deformable portion extending from the gasket pressing portion in a proximal end direction;

wherein the flange attachment member comprises an attachment member body portion having a through hole into which the deformable portion is inserted;

wherein the deformable portion comprises:
- an engagement portion arranged at a proximal end portion of the deformable portion and engaged with the attachment member body portion, and
- an abutment portion arranged at a position different from the engagement portion;

wherein the biasing member is arranged in a compressed state between the gasket pressing member and the flange attachment member by engagement between the engagement portion of the deformable portion and the attachment member body portion of the flange attachment member;

wherein the engagement between the engagement portion of the deformable portion and the attachment member body portion is releasable by deformation of the deformable portion; and wherein the operating member comprises:
- an engagement holding portion that is displaceable from (i) an abutment position at which the engagement holding portion abuts on the abutment portion of the deformable portion to (ii) a separation position at which the engagement holding portion is separated from the abutment portion of the deformable portion, and
- an operating portion configured to displace the operating member with respect to the gasket pressing member such that the engagement holding portion is displaced from the abutment position to the separation position;
- wherein the operation inhibiting member is displaceable with respect to the operating member from (i) an inhibiting position at which the inhibiting portion is engaged with the operating member to (ii) a releasing position at which the engagement between the inhibiting portion and the operating member is released;

wherein, when the engagement holding portion is located at the abutment position, the deformation of the deformable portion is inhibited by abutment between the engagement holding portion and the abutment portion of the deformable portion, and the engagement between the engagement portion of the deformable portion and the attachment member body portion is held; and wherein, when the engagement holding portion is displaced from the abutment position to the separation position by operating the operating portion, the deformation of the deformable portion is allowed by displacing the engagement holding portion from the abutment position to the separation position, the deformable portion is deformed, and the engagement between the engagement portion of the deformable portion and the attachment member body portion is released by biasing force of the biasing member received by the gasket pressing member.

9. The gasket biasing member assembly according to claim 8,
wherein the abutment between the engagement holding portion and the abutment portion of the deformable portion is releasable by pushing the operating member into the gasket pressing member in the distal end direction.

10. The gasket biasing member assembly according to claim 8,
wherein the operating member comprises:
- an extending portion extending in the distal end direction from the operating portion, and
- the engagement holding portion extending in the distal end direction from a distal end of the extending portion and protruding laterally more than the extending portion.

11. The gasket biasing member assembly according to claim 8,
wherein the deformable portion comprises:
- a plurality of deformable body portions,
- an insertion space formed between the plurality of deformable body portions, and
- a plurality of the engagement portions provided at respective proximal end portions of the plurality of deformable body portions and protruding laterally,
wherein each of the plurality of deformable body portions comprises:
- a counter surface facing the insertion space, and
- the abutment portion provided on the counter surface; and
wherein the engagement holding portion of the operating member is inserted into the insertion space.

12. A liquid medicine administration device comprising:
a prefilled syringe comprising:
- an outer cylinder,
- liquid medicine filled inside the outer cylinder, and
- a gasket slidably housed inside the outer cylinder; and
- a biasing member assembly configured to bias the gasket in a distal end direction in order to discharge the liquid medicine;
wherein the outer cylinder comprises:
- a liquid medicine discharge portion located at a distal end portion of the outer cylinder, and
- a flange located at a proximal end portion of the outer cylinder;
wherein the biasing member assembly comprises:
- a gasket pressing member configured to press the gasket in the distal end direction,
- a flange attachment member attached to the flange of the outer cylinder,
- a biasing member configured to bias the gasket pressing member in the distal end direction with respect to the flange attachment member,
- an operating member arranged displaceably with respect to the gasket pressing member, and
- an operation inhibiting member comprising an inhibiting portion configured to inhibit operation of the operating member by being engaged with the operating member;
wherein the gasket pressing member comprises:
- a gasket pressing portion comprising, in a distal end portion, a pressing body portion capable of pressing the gasket in the distal end direction, and
- a deformable portion extending from the gasket pressing portion in a proximal end direction;

wherein the flange attachment member comprises an attachment member body portion having a through hole into which the deformable portion is inserted;

wherein the deformable portion comprises:
an engagement portion arranged at a proximal end portion of the deformable portion and engaged with the attachment member body portion, and
an abutment portion arranged at a position different from the engagement portion and configured to abut on the operating member;

wherein the biasing member is arranged in a compressed state between the gasket pressing member and the flange attachment member by engagement between the engagement portion of the deformable portion and the attachment member body portion of the flange attachment member;

wherein the engagement between the engagement portion of the deformable portion and the attachment member body portion is releasable by deformation of the deformable portion; and wherein the operating member comprises:
an engagement holding portion that is displaceable from (i) an abutment position at which the engagement holding portion abuts on the abutment portion of the deformable portion to (ii) a separation position at which the engagement holding portion is separated from the abutment portion of the deformable portion,
an operating portion configured to displace the operating member with respect to the gasket pressing member such that the engagement holding portion is displaced from the abutment position to the separation position, wherein the operation inhibiting member is displaceable with respect to the operating member from (i) an inhibiting position at which the inhibiting portion is engaged with the operating member to (ii) a releasing position at which engagement between the inhibiting portion and the operating member is released;

wherein, when the engagement holding portion is located at the abutment position, the deformation of the deformable portion is inhibited by abutment between the engagement holding portion and the abutment portion of the deformable portion, and the engagement between the engagement portion of the deformable portion and the attachment member body portion is held; and wherein, when the engagement holding portion is displaced from the abutment position to the separation position by operating the operating portion, the deformation of the deformable portion is allowed by displacing the engagement holding portion from the abutment position to the separation position, the deformable portion is deformed, and the engagement between the engagement portion of the deformable portion and the attachment member body portion is released by biasing force of the biasing member received by the gasket pressing member.

13. The liquid medicine administration device according to claim 12,
wherein the engagement holding portion is configured to be displaced from the abutment position to the separation position by pushing the operating member in the distal end direction with respect to the gasket pressing member.

14. The liquid medicine administration device according to claim 12,
wherein the operating member comprises:
an extending portion extending in the distal end direction from the operating portion, and
the engagement holding portion extending in the distal end direction from a distal end of the extending portion and protruding laterally more than the extending portion.

15. The liquid medicine administration device according to claim 12,
wherein the deformable portion comprises:
a plurality of deformable body portions extending in a proximal end direction from the gasket pressing portion,
an insertion space formed between the plurality of deformable body portions, and
a plurality of the engagement portions provided at respective proximal end portions of the plurality of deformable body portions and protruding laterally outward;
wherein each of the plurality of deformable body portions comprises:
a counter surface facing the insertion space, and
the abutment portion provided on the counter surface; and
wherein the engagement holding portion of the operating member is inserted into the insertion space and abuts on the abutment portion in the abutment position.

16. The liquid medicine administration device according to claim 12,
wherein, when the gasket pressing member is moved by the biasing force of the biasing member in the distal end direction with respect to the flange attachment member, the operating member is moved together with the gasket pressing member.

17. The liquid medicine administration device according to claim 12,
wherein the abutment between the engagement holding portion and the abutment portion of the deformable portion is releasable by pushing the operating member in the distal end direction with respect to the gasket pressing member;
wherein the operating member comprises:
an extending portion extending from the operating portion in the distal end direction, and
an operation engagement portion arranged between the operating portion and the extending portion and protruding laterally more than the extending portion;
wherein the operation inhibiting member includes an insertion port into which the extending portion of the operating member is inserted;
wherein the insertion port comprises:
a first opening having a width smaller than a width of the operation engagement portion, and
a second opening communicating with the first opening and having a width larger than the width of the operation engagement portion;
wherein, when the operation inhibiting member is located at the inhibiting position, the extending portion of the operating member is inserted into the first opening, and an edge portion of the first opening is engaged with the operation engagement portion and functions as the inhibiting portion; and
wherein, when the operation inhibiting member is located at the releasing position, the extending portion of the operating member is inserted into the second opening, the engagement portion is located at a position facing the second opening, and the operating member is pushable in the distal end direction with respect to the gasket pressing member.

\* \* \* \* \*